United States Patent
Echauz et al.

(10) Patent No.: US 7,177,674 B2
(45) Date of Patent: Feb. 13, 2007

(54) PATIENT-SPECIFIC PARAMETER SELECTION FOR NEUROLOGICAL EVENT DETECTION

(76) Inventors: Javier Echauz, 10933 Crabapple Rd. #101, Roswell, GA (US) 30075; Rosana Esteller, 10933 Crabapple Rd. #101, Roswell, GA (US) 30075; Thomas K. Tcheng, 255 Santa Ana Ct., Sunnyvale, CA (US) 94085; Benjamin D. Pless, 255 Santa Ana Ct., Sunnyvale, CA (US) 94085

( * ) Notice: Subject to any disclaimer, the term of this patent is extended or adjusted under 35 U.S.C. 154(b) by 392 days.

(21) Appl. No.: 10/146,663

(22) Filed: May 13, 2002

(65) Prior Publication Data
US 2003/0073917 A1 Apr. 17, 2003

Related U.S. Application Data

(63) Continuation-in-part of application No. 09/977,052, filed on Oct. 12, 2001.

(51) Int. Cl.
*A61B 5/0476* (2006.01)

(52) U.S. Cl. .......................................... 600/544; 607/45
(58) Field of Classification Search ............. 607/45–46, 607/60; 600/544
See application file for complete search history.

(56) References Cited

U.S. PATENT DOCUMENTS

| | | | | |
|---|---|---|---|---|
| 6,353,754 B1 | * | 3/2002 | Fischell et al. | 600/544 |
| 6,473,639 B1 | * | 10/2002 | Fischell et al. | 600/544 |
| 6,480,743 B1 | * | 11/2002 | Kirkpatrick et al. | 607/45 |
| 6,658,287 B1 | * | 12/2003 | Litt et al. | 600/544 |
| 2003/0004428 A1 | * | 1/2003 | Pless et al. | 600/544 |

* cited by examiner

*Primary Examiner*—Carl Layno

(57) ABSTRACT

An epileptiform activity patient-specific template creation system permits a user to efficiently develop an optimized set of patient-specific parameters for epileptiform activity detection algorithms. The epileptiform activity patient template creation system is primarily directed for use with an implantable neurostimulator system having EEG storage capability, in conjunction with a computer software program operating within a computer workstation having a processor, disk storage and input/output facilities for storing, processing and displaying patient EEG signals. The implantable neurostimulator is operative to store records of EEG data when neurological events are detected, when it receives external commands to record, or at preset or arbitrary times. The computer workstation operates on stored and uploaded records of EEG data to derive the patient-specific templates via a single local minimum variant of a multidimensional greedy line search process and a feature overlay process.

51 Claims, 20 Drawing Sheets

PATIENT-SPECIFIC PARAMETER SELECTION FOR NEUROLOGICAL EVENT DETECTION

CROSS-REFERENCE TO RELATED APPLICATION

This is a continuation-in-part of U.S. application Ser. No. 09/977,052, filed on Oct. 12, 2001.

FIELD OF THE INVENTION

This invention relates to analyzing electrographic signals from human patients, and more particularly to systems and methods for developing patient-specific templates for identifying epileptiform activity in a patient's electrographic signals based on short records of collected electrographic data.

BACKGROUND OF THE INVENTION

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. It is believed that as many as two to four million Americans may suffer from various forms of epilepsy. Research has found that its prevalence may be even greater worldwide, particularly in less economically developed nations, suggesting that the worldwide figure for epilepsy sufferers may be in excess of one hundred million.

Because epilepsy is characterized by seizures, its sufferers are frequently limited in the kinds of activities they may participate in. Epilepsy can prevent people from driving, working, or otherwise participating in much of what society has to offer. Some epilepsy sufferers have serious seizures so frequently that they are effectively incapacitated.

Furthermore, epilepsy is often progressive and can be associated with degenerative disorders and conditions. Over time, epileptic seizures often become more frequent and more serious, and in particularly severe cases, are likely to lead to deterioration of other brain functions (including cognitive function) as well as physical impairments.

The current state of the art in treating neurological disorders, particularly epilepsy, typically involves drug therapy and surgery. The first approach is usually drug therapy.

A number of drugs are approved and available for treating epilepsy, such as sodium valproate, phenobarbital/primidone, ethosuximide, gabapentin, phenytoin, and carbamazepine, as well as a number of others. Unfortunately, those drugs typically have serious side effects, especially toxicity, and it is extremely important in most cases to maintain a precise therapeutic serum level to avoid breakthrough seizures (if the dosage is too low) or toxic effects (if the dosage is too high). The need for patient discipline is high, especially when a patient's drug regimen causes unpleasant side effects the patient may wish to avoid.

Moreover, while many patients respond well to drug therapy alone, a significant number (at least 20–30%) do not. For those patients, surgery is presently the best-established and most viable alternative course of treatment.

Currently practiced surgical approaches include radical surgical resection such as hemispherectomy, corticectomy, lobectomy and partial lobectomy, and less-radical lesionectomy, transection, and stereotactic ablation. Besides being less than fully successful, these surgical approaches generally have a high risk of complications, and can often result in damage to eloquent (i.e., functionally important) brain regions and the consequent long-term impairment of various cognitive and other neurological functions. Furthermore, for a variety of reasons, such surgical treatments are contraindicated in a substantial number of patients. And unfortunately, even after radical brain surgery, many epilepsy patients are still not seizure-free.

Electrical stimulation is an emerging therapy for treating epilepsy. However, currently approved and available electrical stimulation devices apply continuous electrical stimulation to neural tissue surrounding or near implanted electrodes, and do not perform any detection—they are not responsive to relevant neurological conditions.

The NeuroCybernetic Prosthesis (NCP) from Cyberonics, for example, applies continuous electrical stimulation to the patient's vagus nerve. This approach has been found to reduce seizures by about 50% in about 50% of patients. Unfortunately, a much greater reduction in the incidence of seizures is needed to provide clinical benefit. The Activa device from Medtronic is a pectorally implanted continuous deep brain stimulator intended primarily to treat Parkinson's disease; it has also been tested for epilepsy. In operation, it supplies a continuous electrical pulse stream to a selected deep brain structure where an electrode has been implanted.

Continuous stimulation of deep brain structures for the treatment of epilepsy has not met with consistent success. To be effective in terminating seizures, it is believed that one effective site where stimulation should be performed is near the focus of the epileptogenic region of the brain. The focus is often in the neocortex, where continuous stimulation may cause significant neurological deficit with clinical symptoms including loss of speech, sensory disorders, or involuntary motion. Accordingly, research has been directed toward automatic responsive epilepsy treatment based on a detection of imminent seizure.

A typical epilepsy patient experiences episodic attacks or seizures, which are characterized by periods of abnormal neurological activity. "Epileptiform" activity refers to specific neurological activity associated with epilepsy as well as with an epileptic seizure and its precursors.

Most prior work on the detection and responsive treatment of seizures via electrical stimulation has focused on analysis of electroencephalogram (EEG) and electrocorticogram (ECoG) waveforms. In common usage, the term "EEG" is often used to refer to signals representing aggregate neuronal activity potentials detectable via electrodes applied to a patient's scalp, though the term can also refer to signals obtained from deep in the patient's brain via depth electrodes and the like. Specifically, "ECoGs" refer to signals obtained from internal electrodes near the surface of the brain (generally on or under the dura mater); an ECoG is a particular type of EEG. Unless the context clearly and expressly indicates otherwise, the term "EEG" shall be used generically herein to refer to both EEG and ECoG signals, regardless of where in the patient's brain the electrodes are located.

It is generally preferable to be able to detect and treat a seizure at or near its beginning, or even before it begins. The beginning of a seizure is referred to herein as an "onset." However, it is important to note that there are two general varieties of seizure onsets. A "clinical onset" represents the beginning of a seizure as manifested through observable clinical symptoms, such as involuntary muscle movements or neurophysiological effects such as lack of responsiveness. An "electrographic onset" refers to the beginning of detectable electrographic activity indicative of a seizure. An electrographic onset will frequently occur before the corresponding clinical onset, enabling intervention before the patient suffers symptoms, but that is not always the case. In addition, there are changes in the EEG that occur seconds or even minutes before the electrographic onset that can be identified and used to facilitate intervention before electrographic or clinical onsets occur. This capability would be considered seizure prediction, in contrast to the detection of a seizure or its onset.

Much of the work on seizure detection has focused on the analysis of EEG signals. See, e.g., J. Gotman, Automatic seizure detection: improvements and evaluation, Electroencephalogr. Clin. Neurophysiol. 1990; 76(4):317–24. In a typical time-domain detection system, EEG signals are received by one or more electrodes and then processed by a control module, which then is capable of performing an action (intervention, warning, recording, etc.) when an abnormal event is detected.

In the Gotman system, EEG waveforms are filtered and decomposed into features representing characteristics of interest in the waveforms. One such feature is characterized by the regular occurrence (i.e., density) of half-waves exceeding a threshold amplitude occurring in a specified frequency band between approximately 3 Hz and 20 Hz, especially in comparison to background (non-ictal) activity. When such half-waves are detected, it is believed that seizure activity is occurring. For related approaches, see also H. Qu and J. Gotman, A seizure warning system for long term epilepsy monitoring, Neurology 1995; 45:2250–4; and H. Qu and J. Gotman, A Patient-Specific Algorithm for the Detection of Seizure Onset in Long-Term EEG Monitoring: Possible Use as a Warning Device, IEEE Trans. Biomed. Eng. 1997; 44(2):115–22. See also U.S. Pat. No. 6,016,449 to Fischell et al. and U.S. application Ser. No. 09/896,092, filed on Jun. 28, 2001.

The known approaches to epileptic seizure detection do provide useful information, and in some cases may provide sufficient information for accurate detection and prediction of most imminent epileptic seizures. It is generally difficult, however, to achieve a high rate of success without extensively tuning or calibrating the detection algorithms. Moreover, even when a detection algorithm is believed to be well tuned, it may be subject to detection errors.

Two types of detection errors are generally possible. A false positive, as the term is used herein, refers to a detection of a seizure or onset when no clinical or electrographic seizure is actually occurring or about to occur. Similarly, a false negative herein refers to the failure to detect a seizure or onset when a clinical seizure actually is occurring or shortly will occur.

In most cases, with all known implementations of the known approaches to detecting abnormal seizure activity solely by monitoring and analyzing EEG activity, when a seizure detection algorithm is tuned to catch all seizures, there will be a significant number of false positives.

It has been suggested that it is possible to treat and terminate seizures by applying electrical stimulation to the brain. See, e.g., U.S. Pat. No. 6,016,449 to Fischell et al., H. R. Wagner, et al., Suppression of cortical epileptiform activity by generalized and localized ECoG desynchronization, Electroencephalogr. Clin. Neurophysiol. 1975; 39(5) :499–506; and R. P. Lesser et al., Brief bursts of pulse stimulation terminate afterdischarges caused by cortical stimulation, Neurology 1999; 53(December):2073–81. And as stated above, it is believed to be beneficial to perform this stimulation only when a seizure (or other undesired neurological event) is occurring or about to occur, as inappropriate stimulation may result in the initiation of seizures. While it is currently believed that there are minimal or no side effects to over-treatment via electrical stimulation (e.g., providing stimulation sufficient to terminate a seizure in response to a false positive), the possibility of accidentally initiating a seizure, causing motor or sensory effects, or increasing the patient's susceptibility to seizures must be considered.

Furthermore, it should be noted that a false negative (that is, a seizure that occurs without any warning or treatment from the device) will often cause the patient significant discomfort and detriment. Clearly, false negatives are to be avoided.

Accordingly, to facilitate tuning or calibrating a device capable of detecting and treating epileptic seizures, there is a need to be able to set detection parameters for a variety of detection algorithms based on data received by an implantable neurostimulator. A system and method capable of performing such an action would set and refine parameters to achieve a clinically acceptable detection rate (number of actual seizures caught in comparison to number of actual seizures missed, or false negatives), a clinically acceptable false positive rate (number of seizures incorrectly identified), and clinically acceptable detection delays.

Fischell et al., in U.S. Pat. No. 6,128,538 (referenced above), describes an implantable neurostimulator for responsive treatment of neurological disorders. The Fischell invention further describes the neurostimulator having a seizure detection subsystem and a data recording subsystem capable of recording EEG signals and transferring the stored EEG signals to external equipment. In U.S. patent application Ser. No. 09/517,797, filed on Mar. 2, 2000 and entitled "Neurological Event Detection Using Processed Display Channel Based Algorithms and Devices Incorporating These Procedures," which is hereby incorporated by reference as though set forth in full herein, Fischell and Harwood describe a system for selecting and combining EEG channels with one or more seizure detection algorithms to detect seizures.

In U.S. patent application Ser. No. 09/556,415, filed on Apr. 21, 2000 and entitled "System for the Creation of Patient Specific Templates for Epileptiform Activity Detection", D. Fischell and J. Harwood also describe an iterative technique for allowing simultaneous display of annotated seizure records and an automated system for processing the records to produce a seizure detector template—namely a set of patient-specific detection or prediction parameters. However, the technique disclosed is not adapted for use with multiple short EEG records uploaded from an implantable device with limited storage capacity. Also Fischell and Harwood do not describe a means for choosing which template is preferred from a plurality of templates, and do not address template development or optimization with regard to any neurological event other than seizure onsets.

Neither U.S. patent application Ser. No. 09/556,415 nor U.S. Pat. No. 6,128,538 (both of which are referenced above) specifically addresses a system for optimizing seizure detector parameter settings through processing EEG data recorded by an implantable neurostimulator.

SUMMARY OF THE INVENTION

The present invention is an epileptiform activity patient template development system that allows the physician to efficiently develop an optimized set of patient-specific parameters for one or more epileptiform activity detection algorithms (also referred to herein as "detection tools"). The term "template" is used herein to refer to a set of patient-specific detection parameters developed by a system or method according to the invention. Such a template once created can be downloaded into an implantable device for the detection of neurological events. The epileptiform activity patient template development system utilizes, in one embodiment, a programmer apparatus, which is a computer programmed to receive EEG records from an implantable device, generate and verify a patient-specific event detection template, and transmit the template back to the implantable device. It may also run in conjunction with an EEG monitoring and analysis system such as the Physician's Workstation (PWS) described by Fischell et al. in U.S. Pat. No. 6,016,449. A preferred implementation of such a workstation would be able to interactively communicate with a neurostimulator through its data communication subsystem, in a manner similar to that described by Fischell et al in U.S. Pat. No. 6,016,449.

In many patients, magnetic resonance imaging (MRI), single photon emission computed tomography (SPECT), and other non-invasive imaging systems have been used to successfully localize the focus of the neurological disorder such as the epileptogenic focus in a patient with epilepsy. In other patients, the focus can be identified from the clinical manifestations of the patient's seizures, from scalp EEG measurements, and from intracranial EEG or ECoG measurements. In either case, without long term invasive mapping procedures, it may be desirable to implant the neurostimulator with multiple electrodes in the general areas of interest. After implant there would be some short testing either in the operating room or during the subsequent hospital stay, primarily for patient recovery and for verification and adjustment of device operation, and also to collect EEG data for use according to the invention. Additionally, during the post-operative testing, stimulation could be applied to attempt to induce epileptiform activity. These EEG patterns will be captured by the neurostimulator and uploaded to the programmer. Alternatively, or in addition, it is possible to transfer EEG data from a traditional EEG recording device or workstation to the programmer, if such recordings were made using implanted electrodes (although some data preprocessing may be necessary to do so). Baseline EEG information may be transmitted from the implanted neurostimulator at any time to provide examples of the patient's EEG during sleep and awake states.

An initial detection template that is extremely sensitive to induced epileptiform activity events (or that has been developed based only on baseline activity, for example) may then be developed and downloaded to the neurostimulator. Alternatively, a default detection algorithm that is designed to be very sensitive (but not very specific) across a population of patients may be used. In either case, the patient would then be sent home with the sensitive neurological event detector enabled, but with responsive stimulation disabled. In this mode, the neurostimulator will act as an EEG data collector to save each event detected including the EEG data from a time typically 120 seconds before the detection (also known as "pretrigger"). See also, e.g., U.S. Pat. No. 6,128,538. To allow a reasonable number of events to be recorded, total time allocated for each detection should be between 45 seconds and 300 seconds (5 minutes), i.e. 15 seconds to 150 seconds (2½ minutes) following detection plus 30 to 150 seconds before the detection. It should be noted, however, that the amount of time allocated to recording an event may be dependent in part on the type of event sought to be captured. Because the optimal electrode would not yet be known, the initial recordings would generally be multi-channel in order to identify the electrode pair from which the earliest indication of epileptiform activity can be detected or predicted.

In those cases where the patient or a caregiver observes that a seizure has taken place, it would be possible to save as much as, or more than, the previous 600 seconds (10 minutes) of data by use of a patient initiating device as described in U.S. Pat. No. 6,128,538. Once one or more clinical seizures have occurred, the data would be uploaded to the neurostimulator programmer. The data upload may take place either directly from the neurostimulator to the programmer if the patient visits the clinician, or the data may be uploaded via telephone lines or in a wireless manner either to a database that can communicate with the clinician's programmer or directly to the programmer. The uploaded data will allow selection of a desirable and useful electrode pair or pairs for detection of epileptiform activity. The patient and/or the patient's caregiver is instructed to maintain a seizure log of when observed seizures occur. Diagnostic counters in the device keep track of the time of the triggers that resulted in the storage of the EEG records. As is well documented, seizure logs are not completely accurate and it is not uncommon for as many as half of the seizures that a patient actually experiences to be omitted from the patient's log. However, with the assistance of information in a seizure log, real seizures may be identified by comparing the time at which an EEG record was stored with an entry in the patient's seizure log. The clinician then annotates the onsets, electrographic seizures, and the false positives appropriately for the detection parameter optimization algorithms to operate on. Additional EEG records, baseline or otherwise, may be stored at any time using either a real-time EEG telemetry capability in the implanted neurostimulator, a patient initiating device, or by using the programmer to trigger the storage of an EEG record. The more baseline data that is available, the better the performance of the detector can be expected to be. Accordingly, it is important to collect baseline data during alert, drowsy, and sleeping states. Also, analysis of the data using a modification of the automated template creation system described by Fischell and Harwood in application Ser. No. 09/556,415, referenced above, would allow refinement of the "inseizure" detector and creation of a template for the seizure precursor or seizure onset that detects the earliest unique waveform indicative of a coming clinical seizure for each patient.

In one manner of operation, the clinician operates on the stored and uploaded data in the programmer to arrive at detection parameters based on the stored EEG records. In another manner of operation, the EEG records may be stored in the programmer, but are also uploaded to a centralized database. The database may automatically analyze the data, or a person with clinical skill may analyze the data. In either case, the patient's clinician may be provided with the identified detection parameters, preferably via a computer network (e.g., an intranet or the Internet) or some other digital data link. If the database approach is used, the seizure log information is preferably uploaded to the database with the EEG records by having the communication be performed through a personal digital assistant (PDA) such as a Palm Pilot® or other portable computer. The PDA can then be used to store and transfer the seizure log information (as well as quality of life, or QOL, information).

The new detector parameters (derived from the stored EEG records containing at least one example of a seizure) would then be downloaded to the neurostimulator. The patient would then begin the second phase of seizure data collection with a reduced number of electrode pairs being used for data collection (typically only one or two). This will allow more EEG records to be stored in the neurostimulator. With the use of the patient initiating device to store an EEG, few seizures will be missed. If the device has already detected and initiated storage of the seizure EEG, then the patient command will be saved in memory but not executed.

After a period of time during which there have been one or more clinical seizures, the data will once more be uploaded from the neurostimulator to the programmer (or database) for analysis. Using the multiple EEG records from this phase and previous phases, the onset and in-seizure detector parameters can further be refined to ignore any of the "false positive" detections that were captured but were not, in fact, related to an electrographic or clinical seizure. The revised set of onset, electrographic seizure, and other event detection parameters and the choice of the desired electrode pairs are then downloaded to the neurostimulator.

Additional phases like the second phase above may be then initiated to confirm and/or further refine the accuracy of the new detectors if needed.

While one embodiment of the invention is adapted to detect (and optimize the detection of) seizure and onset events, it should also be noted that it is also possible and desirable to perform prediction, or the identification of a high likelihood of a seizure, either clinical or electrographic, based on the detection of particular electrographic patterns before any identifiable specific onset or seizure activity. This can be accomplished by analyzing EEG records occurring before seizures with one or more detection algorithms to identify waveform characteristics of interest.

When the physician is confident of the sensitivity and specificity of the detector(s) and/or a waiting period has concluded, the stimulation subsystem of the neurostimulator can be enabled so that the next detected onset, electrographic seizure, predicted seizure, or other event will produce a responsive stimulation to previously selected electrodes.

In the final revision of detector parameters, all previous phase seizure and baseline data that were uploaded to the programmer and/or database may be used in a simulation to verify the performance of the detectors. A detector like the one described by Fischell and Harwood in application Ser. No. 09/517,797, referenced above, could be suitable for this purpose. Even during the stimulation phase, combined use of onset and in-seizure detectors as described by Fischell and Harwood will identify an electrographic seizure where the precursor (onset) is missed. Uploads of the stored EEG records from these events will allow the physician to update the onset detection template as needed. If the responsive stimulation is ineffective following an accurate onset or in-seizure detection, then the stored EEG will help the physician to know what happened and allow the physician to adjust the stimulation parameters to be more effective. The amount of EEG data stored may be different for an onset detector in comparison to an in-seizure detector. For example, more data from before a detection should generally be stored if a seizure is detected by the in-seizure detector. This is because an in-seizure detector will generally be triggered some time after a seizure onset has already passed, and to enable capturing a sufficient amount of pre-onset EEG data, the amount of data stored from before the in-seizure detector triggered should be relatively increased.

Ongoing storage of correctly detected epileptiform activity and false positives allows for ongoing refinement of the onset and seizure detectors. Furthermore, if the patient's medical condition changes, the stored EEGs allow for rapid adjustment of the detectors to suit the patient's changing condition.

Another aspect of the present invention is to save EEG data when a seizure is recognized by the patient or the patient's caregiver. For example, if during treatment with the stimulator enabled, the seizure detection is missed and a clinical seizure occurs, the patient or the patient's caregiver can use the patient initiating device to tell the neurostimulator to save the preceding X seconds of EEG data so that the physician can adjust the seizure detector template to avoid missing future seizures or seizure onsets. The value of X can be set by the physician using the system programmer to be between 30 seconds and 1,800 seconds (30 minutes). If seizure prediction algorithms are being used, a longer storage time may be desirable. If the onset occurs in the 30 seconds before clinical seizure, then a shorter period of time is acceptable.

In application Ser. No. 09/556,415, Fischell and Harwood describe an iterative technique for automated template development for a seizure detector. That technique contemplates having hours of data without seizure activity to act as a baseline to test for false positive detections. The present invention envisions creating a baseline data set from multiple relatively short EEG records recorded by the implanted neurostimulator. In addition, as described above, Fischell and Harwood do not describe a means for choosing a preferred template from a plurality of templates.

The present invention in one embodiment uses selectable criteria to search and sort the possible detection templates, allowing the user some choice among advantageous templates. In one embodiment of the invention, only those templates with no false positive detections are available for use (as long as at least one such template has been found), and the template choices are sorted on the basis of average latency to detection.

The present invention alternatively envisions user choice from a range of potentially useful templates where disallowing false positives while risking missing a real seizure (most restrictive, i.e. highly specific, but not very sensitive) is at one end of the range, and allowing false positives but never missing a real seizure (least restrictive, i.e. highly sensitive, but not very specific) is at the other. In terms of the automated template development software used on the limited quantity of data collected by the neurostimulator, a number of sets of parameters may be able to accurately find all the seizures with no false positives. The most restrictive parameters will typically result in the fewest number of detections of a pattern representing each seizure. The least restrictive will typically have many detections of the desired waveform pattern. The ideal settings are generally neither the most restrictive nor the least restrictive, but are in between those limits, e.g. a template that provides the best specificity and sensitivity, and the shortest latency to detection of each seizure.

Additionally, the programmer may generate additional data from the data sets uploaded from the implanted neurostimulator. The stored EEGs of known seizures (as annotated by the clinician) can be slightly modified to make new data sets. Useful modifications include varying the amplitude by typically 20%, changing the "playback speed" by typically 10%, adding a random noise signal having an energy content of typically 20% of the data set, or a combination of these and similar modifications. The result is a much larger dataset including these data surrogates, facilitating the generation of a set of detection parameters that maintains high sensitivity, but is more specific than a set of detection parameters generated from the one or few real seizures recorded.

Noise is another confounding signal that may adversely affect the efficacy of automatic epileptiform activity detection. Rather than wait for the patient to experience noise, it is anticipated that stereotypical noise records may be included in the training set of data to arrive at detection parameters that are capable of discriminating noise from neurological events. Typical sources of electrographic noise include cellular telephones, fluorescent and other gas discharge lighting, welders, electric motors, RF amplifiers, electronic theft detectors, and AC power lines. Stored EEG records generated in controlled environments, or recorded by a different patient, may be added to a patient's data set of stored EEGs to improve the detection parameters, or simulated noise signals may be superimposed onto the patient's stored EEG records prior to or during template generation.

The choice as to how restrictive the detector template should be must be based on the physician's estimate of how likely it is that a stimulation caused by a false positive will induce a seizure or other undesired side effect. Fortunately, this can be tested by programmer commanded stimulation during implantation or at any time after implantation. If the proposed stimulation does not induce epileptiform activity or cause sensory or motor effects, then a less restrictive setting for the detection template may be used.

Once the responsive stimulator is enabled, the patient or the patient's caregiver should use the initiating device to signal the neurostimulator any time an actual seizure occurs or has occurred. In theory, if the seizure resulted from either a false positive having been stimulated (a stimulation induced seizure) or because the detector failed to identify the onset and the seizure, the EEG data stored will capture any changes in the patient's epileptiform activity to allow modification of the seizure detector template. However, it should be noted that if a detection causes stimulation to occur and epileptiform activity occurs thereafter, it may be difficult to determine whether the original detection was a false positive (with the epileptiform activity initiated by the stimulation) or a correct positive (with the epileptiform activity arising out of the detected onset). This kind of situation is best identified in a monitoring and detection context with stimulation disabled. If the electrographic seizure was properly detected but the stimulation failed to stop it, changes may be made in the stimulation parameters to attempt to stop future seizures with greater efficacy.

It should be noted that a single patient may present with multiple onset and/or seizure types, as well as multiple seizure foci. In any of these cases, the clinician may elect to sort the onsets and/or seizures into self-similar groups, annotate them as separate types of events using the programmer, and derive detection parameters separately for each group. Data from different seizure foci may also be handled separately. Likewise, detection parameters may be derived specifically to detect certain types of noise to reduce the probability of false positives caused by the noise.

Certain aspects of the present invention are envisioned as residing as software, firmware, or other code in the programmer (or physician's workstation) for the neurostimulator, and in the database as described above.

As used herein, it should be noted that the terms "detection parameters" and "template" are used interchangeably; a template as used in a system according to the invention would be considered a set of detection parameters. Similarly, as set forth above, the terms "EEG" and "ECoG" are both used to refer to electrographic activity measured from the patient's brain, and are used interchangeably herein.

Thus, it is an object of this invention to provide a highly sensitive epileptiform activity detection template to capture EEG records with an implantable device, where such EEG records represent electrographic seizures, false positive detections, and normal baseline data not causing false positives, providing a basis for deriving patient-specific epileptiform activity detection parameters.

Another object of this invention is to provide a set of patient-specific epileptiform detection parameters (a "template") by automatically processing stored EEG records containing epileptiform and non-epileptiform events.

Another object of this invention is to provide for associating stored EEG records with clinical seizures identified by the patient or caregiver (typically in a seizure log, either in written form or created in a PDA or some other means of collecting data suitable for transmission to a database).

Another object of this invention is to utilize a centralized database system to transfer EEG records from one or more programmers to the database, and from the database to the programmers. The centralized database system may also transfer onset and seizure detection parameters to the database and to the programmers. The centralized database system may also receive seizure log information to correlate with stored EEG records and QOL information.

Another object of this invention is to use data generation techniques to generate additional EEG records from a smaller number of actual EEG records stored.

Another object of this invention is to provide to the template development system artificial or transformed EEG data representative of EEG records containing noise from various types of noise sources.

Another object of this invention is to provide an epileptiform activity patient template development system that can simultaneously provide for the analysis of, and ultimately analyze a multiplicity of EEG records stored by an implantable neurostimulator.

Another object of this invention is to provide a template creation system that can simultaneously display a multiplicity of stored EEG records from one or more uploads from an implantable neurostimulator.

Still another object of the present invention is to provide the capability to annotate electrographic onsets, seizures and/or other events within the multiplicity of EEG records.

Still another object of this invention is to provide an automated system to process the multiplicity of EEG records to identify sets of seizure detector parameters that detect as many true clinical seizures or onsets to true clinical seizures as possible with a minimum number of false positive detections within the multiplicity of EEG records.

Still another object of the present invention is to provide a ranking of seizure parameter templates from those found to have no false negatives and no false positives on the limited set of EEG records analyzed.

Still another object of the present invention is to have the ranking based on the number of detected onset or seizure waveforms within a preset time from the annotated onset or seizure start.

Still another object of the present invention is to have the ranking based on the average time from the annotated onset or seizure start to the first detection of the onset or seizure waveform pattern.

Yet another object of the present invention is to have the ranking based on a physician's input of how restrictive the onset and/or seizure detector should be.

Yet another object of the present invention is to have a method for iteratively processing multiple stored EEG records from an implantable neurostimulator to refine the seizure detector template.

Yet another object of the present invention is to have the neurostimulator store a longer EEG record when activated with a patient initiating device to indicate a clinical seizure has occurred.

Yet another object of the present invention is to have the neurostimulator store baseline EEG records for false positive testing by the template development system.

Yet another object is to have a neurostimulator system optimized for the detection of seizures, seizure onsets, seizure precursors, events predictive of seizures, other neurological events of interest, and noise.

These and other objects and advantages of this invention will become apparent to a person of ordinary skill in this art upon careful reading of the detailed description of this invention including the drawings as presented herein.

BRIEF DESCRIPTION OF THE DRAWINGS

These and other objects, features, and advantages of the invention will become apparent from the detailed description below and the accompanying drawings, in which.

DETAILED DESCRIPTION OF THE INVENTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 1:
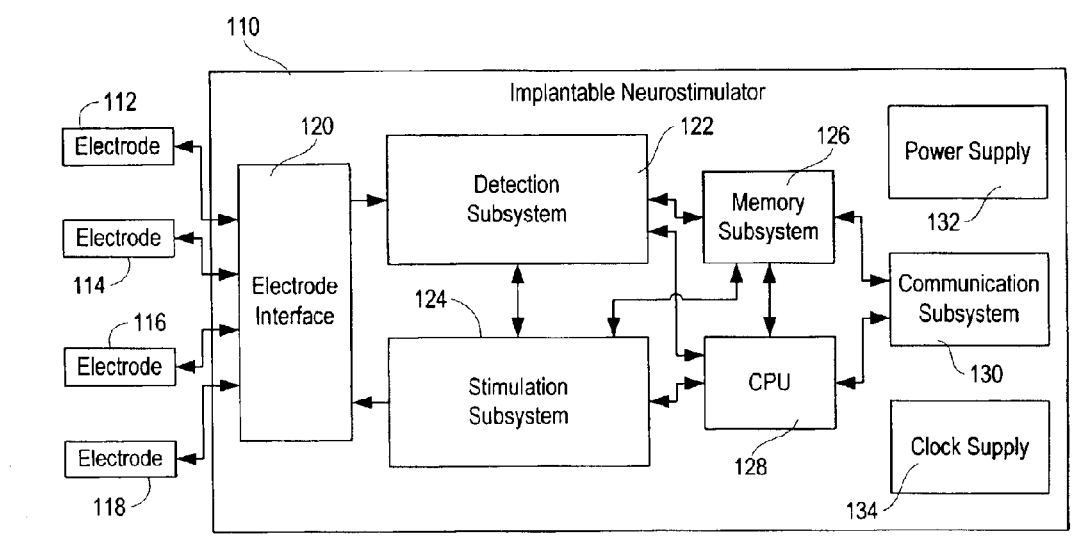
FIG. 1 is a block diagram of an implantable neurostimulator for responsive treatment of neurological disorders.

FIG. 1 depicts a schematic block diagram of a neurostimulator system according to the invention, including an implantable neurostimulator 110, which in one embodiment is a small self-contained responsive neurostimulator that is intracranially implanted. As the term is used herein, a responsive neurostimulator is a device capable of detecting ictal activity (or other neurological events) and providing electrical stimulation to neural tissue in response to that activity, where the electrical stimulation is specifically intended to terminate the ictal activity, treat a neurological event, prevent an unwanted neurological event from occurring, or lessen the severity or frequency of certain symptoms of a neurological disorder. As disclosed herein, the responsive neurostimulator detects ictal activity by systems and methods according to the invention and according to patient-specific templates as disclosed herein.

It should be recognized that the embodiment of the device described and illustrated herein is preferably a responsive neurostimulator for detecting and treating epilepsy by detecting seizure precursors and preventing and/or terminating epileptic seizures.

In an alternative embodiment of the invention, the device is not a responsive neurostimulator, but is an apparatus capable of detecting neurological conditions and events and performing actions in response thereto. The actions performed by such an embodiment of the device need not be therapeutic, but may involve data recording or transmission, providing warnings to the patient, or any of a number of known alternative actions. Such a device will typically act as a diagnostic device when interfaced with external equipment, as will be discussed in further detail below.

FIG. 1 is an overall block diagram of the implantable neurostimulator 110 used for measurement, detection, and treatment according to the invention. Inside the housing of the neurostimulator 110 are several subsystems making up the device. The implantable neurostimulator 110 is capable of being coupled to a plurality of electrodes 112, 114, 116, and 118 (each of which may be individually or together connected to the implantable neurostimulator 110 via one or more leads) for sensing and stimulation. In the illustrated embodiment, the coupling is accomplished through a lead connector. Although four electrodes are shown in FIG. 1, it should be recognized that any number is possible, and in the embodiment described in detail below, eight electrodes are used. In fact, it is possible to employ an embodiment of the invention that uses a single lead with at least two electrodes, or two leads each with a single electrode (or with a second electrode provided by a conductive exterior portion of the housing in one embodiment), although bipolar sensing between two closely spaced electrodes on a lead is preferred to minimize common mode signals including noise.

The electrodes 112–118 are in contact with the patient's brain or are otherwise advantageously located to receive EEG signals or provide electrical stimulation. Each of the electrodes 112–118 is also electrically coupled to an electrode interface 120. Preferably, the electrode interface is capable of selecting each electrode as required for sensing and stimulation; accordingly the electrode interface is coupled to a detection subsystem 122 and a stimulation subsystem 124. The electrode interface may also provide any other features, capabilities, or aspects, including but not limited to amplification, isolation, and charge-balancing functions, that are required for a proper interface with neurological tissue and not provided by any other subsystem of the device 110.

The detection subsystem 122 includes and serves primarily as an EEG waveform analyzer; detection is accomplished in conjunction with a central processing unit (CPU) 128. The EEG waveform analyzer function is adapted to receive EEG signals from the electrodes 112–118, through the electrode interface 120, and to process those EEG signals to identify neurological activity indicative of a seizure or a precursor to a seizure. One way to implement such EEG analysis functionality is disclosed in detail in U.S. Pat. No. 6,016,449 to Fischell et al., incorporated by reference above. Additional inventive methods are described in U.S. patent application Ser. No. 09/896,092 to Pless et al., filed on Jun. 28, 2001 and entitled "SEIZURE SENSING AND DETECTION USING AN IMPLANTABLE DEVICE," of which details will be set forth below. The detection subsystem may optionally also contain further sensing and detection capabilities, including but not limited to parameters derived from other physiological conditions (such as electrophysiological parameters, temperature, blood pressure, etc.). In general, prior to analysis, the detection subsystem performs amplification, analog to digital conversion, and multiplexing functions on the signals in the sensing channels received from the electrodes 112–118.

The stimulation subsystem 124 is capable of applying electrical stimulation to neurological tissue through the electrodes 112–118. This can be accomplished in any of a number of different manners. For example, it may be advantageous in some circumstances to provide stimulation in the form of a substantially continuous stream of pulses, or on a scheduled basis. Preferably, therapeutic stimulation is provided in response to abnormal events detected by the EEG analyzer function of the detection subsystem 122. As illustrated in FIG. 1, the stimulation subsystem 124 and the EEG analyzer function of the detection subsystem 122 are in communication; this facilitates the ability of stimulation subsystem 124 to provide responsive stimulation as well as an ability of the detection subsystem 122 to blank the amplifiers while stimulation is being performed to minimize stimulation artifacts. It is contemplated that the parameters of the stimulation signal (e.g., frequency, duration, waveform) provided by the stimulation subsystem 124 would be specified by other subsystems in the implantable neurostimulator 110, as will be described in further detail below.

In accordance with the invention, the stimulation subsystem 124 may also provide for other types of stimulation, besides electrical stimulation described above. In particular, in certain circumstances, it may be advantageous to provide audio, visual, or tactile signals to the patient, to provide somatosensory electrical stimulation to locations other than the brain, or to deliver a drug or other therapeutic agent (either alone or in conjunction with stimulation).

Also in the implantable neurostimulator 110 is a memory subsystem 126 and the CPU 128, which can take the form of a microcontroller. The memory subsystem is coupled to the detection subsystem 122 (e.g., for receiving and storing data representative of sensed EEG signals and evoked responses), the stimulation subsystem 124 (e.g., for providing stimulation waveform parameters to the stimulation subsystem), and the CPU 128, which can control the operation of the memory subsystem 126. In addition to the memory subsystem 126, the CPU 128 is also connected to the detection subsystem 122 and the stimulation subsystem 124 for direct control of those subsystems.

Also provided in the implantable neurostimulator 110, and coupled to the memory subsystem 126 and the CPU 128, is a communication subsystem 130. The communication subsystem 130 enables communication between the device 110 and the outside world, particularly an external programmer and a patient initiating device, both of which will be described below with reference to FIG. 2. As set forth above, the disclosed embodiment of the communication subsystem 130 includes a telemetry coil (which may be situated outside of the housing of the implantable neurostimulator 110) enabling transmission and reception of signals, to or from an external apparatus, via inductive coupling. Alternative embodiments of the communication subsystem 130 could use an antenna for an RF link or an audio transducer for an audio link. Preferably, the communication subsystem 130 also includes a GMR (giant magnetoresistive effect) sensor to enable receiving simple signals (namely the placement and removal of a magnet) from a patient initiating device; this capability can be used to initiate EEG recording as will be described in further detail below.

If the stimulation subsystem 124 includes the audio capability set forth above, it may be advantageous for the communication subsystem 130 to cause the audio signal to be generated by the stimulation subsystem 124 upon receipt of an appropriate indication from the patient initiating device (e.g., the magnet used to communicate with the GMR sensor of the communication subsystem 130), thereby confirming to the patient or caregiver that an EEG record will be stored.

Rounding out the subsystems in the implantable neurostimulator 110 are a power supply 132 and a clock supply 134. The power supply 132 supplies the voltages and currents necessary for each of the other subsystems. The clock supply 134 supplies substantially all of the other subsystems with any clock and timing signals necessary for their operation, including a real-time clock signal to coordinate programmed and scheduled actions.

It should be observed that while the memory subsystem 126 is illustrated in FIG. 1 as a separate functional subsystem, the other subsystems may also require various amounts of memory to perform the functions described above and others. Furthermore, while the implantable neurostimulator 110 is preferably a single physical unit (i.e., a control module) contained within a single implantable physical enclosure, namely the housing described above, other embodiments of the invention might be configured differently. The neurostimulator 110 may be provided as an external unit not adapted for implantation, or it may comprise a plurality of spatially separate units each performing a subset of the capabilities described above, some or all of which might be external devices not suitable for implantation. Also, it should be noted that the various functions and capabilities of the subsystems described above may be performed by electronic hardware, computer software (or firmware), or a combination thereof. The division of work between the CPU 128 and the other functional subsystems may also vary—the functional distinctions illustrated in FIG. 1 may not reflect the integration of functions in a real-world system or method according to the invention.

Figure 2:
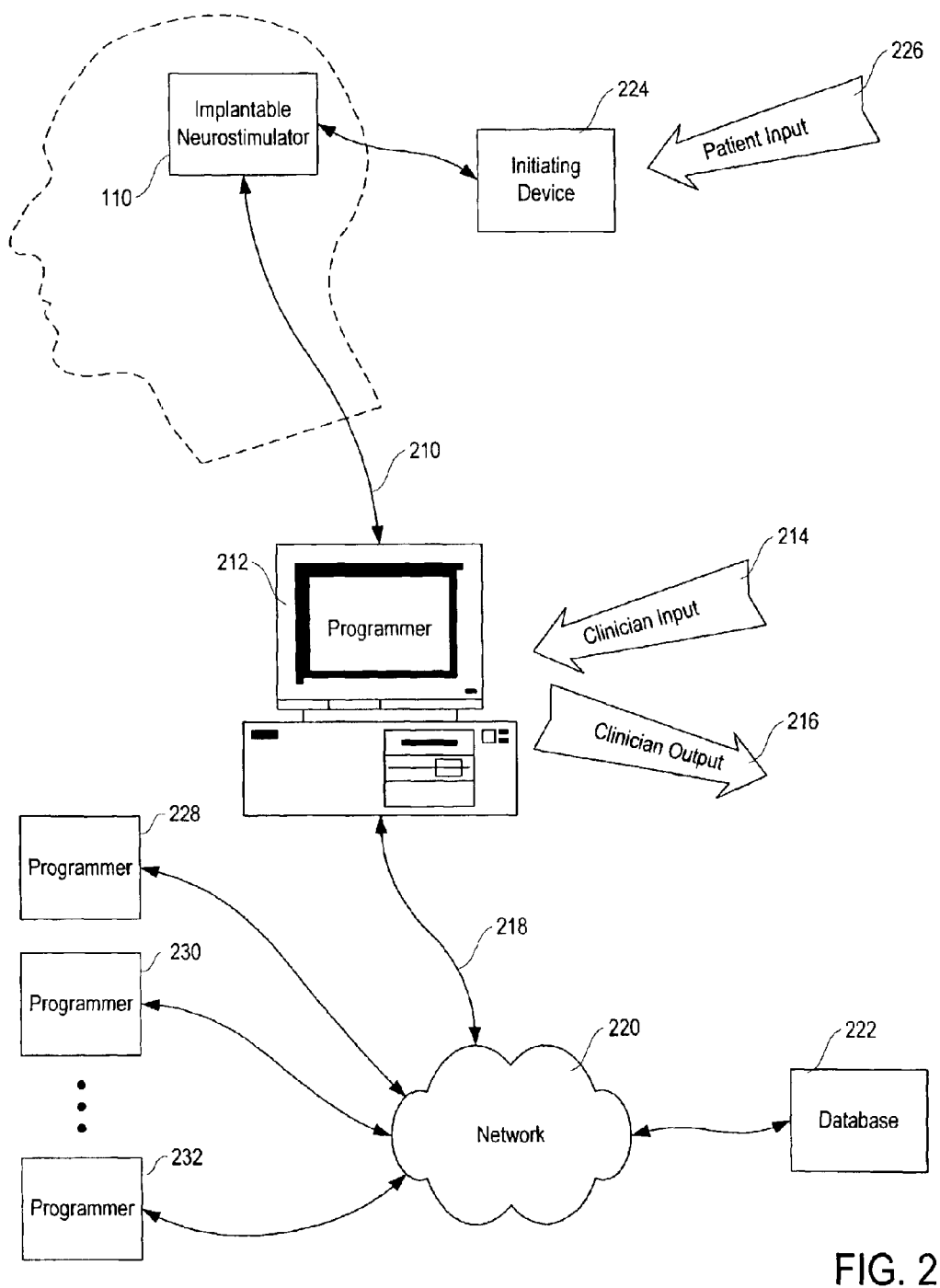
FIG. 2 is a block diagram of an implantable neurostimulator system used in conjunction with external equipment.

As stated above, and as illustrated in FIG. 2, a neurostimulator according to the invention operates in conjunction with external equipment. The implantable neurostimulator 110 is mostly autonomous (particularly when performing its usual sensing, detection, and stimulation capabilities), but preferably includes a selectable part-time wireless link 210 to external equipment such as a programmer 212. In the disclosed embodiment of the invention, the wireless link 210 is established by moving a wand (or other apparatus) having communication capabilities and coupled to the programmer 212 into communication range of the implantable neurostimulator 110. The programmer 212 can then be used to manually control the operation of the device, as well as to transmit information to or receive information from the implantable neurostimulator 110. Several specific capabilities and operations performed by the programmer 212 in conjunction with the device will be described in further detail below.

The programmer 212 is capable of performing a number of advantageous operations in connection with the invention. In particular, the programmer 212 is able to specify and set variable parameters in the implantable neurostimulator 110 to adapt the function of the device to meet the patient's needs, upload or receive data (including but not limited to stored EEG waveforms, parameters, or logs of actions taken) from the implantable neurostimulator 110 to the programmer 212, download or transmit program code and other information from the programmer 212 to the implantable neurostimulator 110, or command the implantable neurostimulator 110 to perform specific actions or change modes as desired by a physician operating the programmer 212. To facilitate these functions, the programmer 212 is adapted to receive clinician input 214 and provide clinician output 216; data is transmitted between the programmer 212 and the implantable neurostimulator 110 over the wireless link 210.

The programmer 212 may be used at a location remote from the implantable neurostimulator 110 if the wireless link 210 is enabled to transmit data over long distances. For example, the wireless link 210 may be established by a short-distance first link between the implantable neurostimulator 110 and a transceiver, with the transceiver enabled to relay communications over long distances to a remote programmer 212, either wirelessly (for example, over a wireless computer network) or via a wired communications link (such as a telephonic circuit or a computer network).

The programmer 212 may also be coupled via a communication link 218 to a network 220 such as the Internet. This allows any information uploaded from the implantable neurostimulator 110, as well as any program code or other information to be downloaded to the implantable neurostimulator 110, to be stored in a database 222 at one or more data repository locations (which may include various servers and network-connected programmers like the programmer 212). This would allow a patient (and the patient's physician) to have access to important data, including past treatment information and software updates, essentially anywhere in the world that there is, a programmer (like the programmer 212) and a network connection. Alternatively, the programmer 212 may be connected to the database 222 over a trans-telephonic link.

In yet another alternative embodiment of the invention, the wireless link 210 from the implantable neurostimulator 110 may enable a transfer of data from the neurostimulator 110 to the database 222 without any involvement by the programmer 212. In this embodiment, as with others, the wireless link 210 may be established by a short-distance first link between the implantable neurostimulator 110 and a transceiver, with the transceiver enabled to relay communications over long distances to the database 222, either wirelessly (for example, over a wireless computer network) or via a wired communications link (such as trans-telephonically over a telephonic circuit, or over a computer network).

In the disclosed embodiment, the implantable neurostimulator 110 is also adapted to receive communications from an initiating device 224, typically controlled by the patient or a caregiver. Accordingly, patient input 226 from the initiating device 224 is transmitted over a wireless link to the implantable neurostimulator 110; such patient input 226 may be used to cause the implantable neurostimulator 110 to switch modes (on to off and vice versa, for example) or perform an action (e.g., store a record of EEG data). Preferably, the initiating device 224 is able to communicate with the implantable neurostimulator 110 through the communication subsystem 130 (FIG. 1), and possibly in the same manner the programmer 212 does. The link may be unidirectional (as with the magnet and GMR sensor described above), allowing commands to be passed in a single direction from the initiating device 224 to the implantable neurostimulator 110, but in an alternative embodiment of the invention is bi-directional, allowing status and data to be passed back to the initiating device 224. Accordingly, the initiating device 224 may be a programmable PDA or other hand-held computing device, such as a Palm Pilot® or PocketPC®. However, a simple form of initiating device 224 may take the form of a permanent magnet, if the communication subsystem 130 is adapted to identify magnetic fields and interruptions therein as communication signals.

The implantable neurostimulator 110 (FIG. 1) generally interacts with the programmer 212 (FIG. 2) as described below. Data stored in the memory subsystem 126 can be retrieved by the patient's physician through the wireless communication link 210, which operates through the communication subsystem 130 of the implantable neurostimulator 110. In connection with the invention, a software operating program run by the programmer 212 allows the physician to read out a history of events detected including EEG information before, during, and after each event, as well as specific information relating to the detection of each event (such as, in one embodiment, the time-evolving energy spectrum of the patient's EEG). The programmer 212 also allows the physician to specify or alter any programmable parameters of the implantable neurostimulator 110. The software operating program also includes tools for the analysis and processing of recorded EEG records to assist the physician in developing optimized seizure detection parameters for each specific patient.

In an embodiment of the invention, the programmer 212 is primarily a commercially available PC, laptop computer, or workstation having a CPU, keyboard, mouse and display, and running a standard operating system such as Microsoft Windows®, Linux®, Unix®, or Apple Mac OS®. It is also envisioned that a dedicated programmer apparatus with a custom software package (which may not use a standard operating system) could be developed.

When running the computer workstation software operating program, the programmer 212 can process, store, play back and display on the display the patient's EEG signals, as previously stored by the implantable neurostimulator 110 of the implantable neurostimulator device.

The computer workstation software operating program also has the capability to simulate the detection and prediction of epileptiform activity. Included in the capability to simulate detection of epileptiform activity, the software operating program of the present invention has the capability to allow a clinician to create or modify a patient-specific collection of information comprising, in one embodiment, algorithms and algorithm parameters for epileptiform activity detection. The patient-specific collection of detection algorithms and parameters used for neurological activity detection according to the invention will be referred to herein as a detection template or patient-specific template. The patient-specific template, in conjunction with other information and parameters generally transferred from the programmer to the implanted device (such as stimulation parameters, time schedules, and other patient-specific information), make up a set of operational parameters for the neurostimulator.

Following the development of a patient specific template on the workstation 212, the patient-specific template would be downloaded through the communications link 210 from the programmer 212 to the implantable neurostimulator 110.

The patient-specific template is used by the detection subsystem 122 and the CPU 128 of the implantable neurostimulator 110 to detect epileptiform activity in the patient's EEG signals, which can be programmed by a clinician to result in responsive stimulation of the patient's brain, as well as the storage of EEG records before and after the detection, facilitating later clinician review.

Preferably, the database 222 is adapted to communicate over the network 220 with multiple programmers, including the programmer 212 and additional programmers 228, 230, and 232. It is contemplated that programmers will be located at various medical facilities and physicians' offices at widely distributed locations. Accordingly, if more than one programmer has been used to upload EEG records from a patient's implantable neurostimulator 110, the EEG records will be aggregated via the database 222 and available thereafter to any of the programmers connected to the network 220, including the programmer 212.

Figure 3:
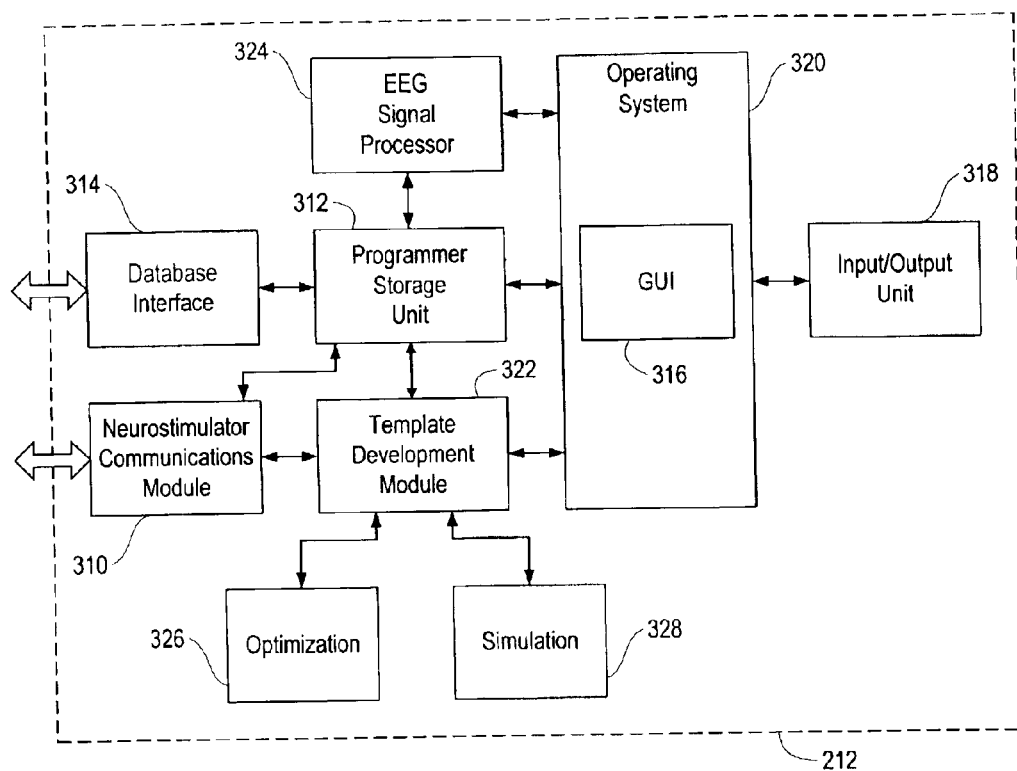
FIG. 3 is a block diagram of a programmer for use in an implantable neurostimulator system and for creating patient-specific templates according to the invention.

FIG. 3 illustrates the functional architecture of the programmer 212, including modules of its operating program. As used herein, the term "module" may refer to a unit of software, firmware, or other computer code that carries out a specific function; a code module may include processes, subroutines, libraries and other modules. However, it should be noted that the functional distinctions illustrated in FIG. 3 are not necessarily representative of separate code modules, and are set forth as shown to indicate the separate functions required of the programmer 212.

EEG data from the implantable neurostimulator 110 (FIG. 1) is received by the programmer 212 (FIG. 2) via a neurostimulator communications module 310 and transferred to a programmer storage unit 312 for analysis and for optional eventual long-term storage in the EEG record database 222 (FIG. 2). The programmer interfaces with the database 222 via a database interface 314, which provides the functionality of the data link 218.

A graphical user interface (GUI) 316 provides user control of the programmer software program through menus and toolbars shown on a display portion of an input/output unit 318 and selected with a keyboard and/or a pointing device such as a mouse or trackball. The GUI 316 provides menus, dialog boxes, tool bars, and the like to control the various components of the programmer 212 and the software program. An operating system 320 performs various tasks necessary operation of the programmer, and establishes the available functions and elements of the GUI 316.

The programmer 212 is designed to analyze and process EEG data that has been transferred from the implantable neurostimulator 110 (FIG. 1) and stored in the programmer storage unit 312. In addition, stored EEG data files stored in the EEG database 222 (FIG. 2) may come from a separate EEG data acquisition system (not shown) that may include data collected during the initial diagnosis of the patient. Further stored EEG data files may come from other sources, including EEG data records transmitted telephonically or wirelessly, either directly from the implantable device 10 or indirectly through a PDA or other patient-controlled apparatus, to the database 222, thereby avoiding the programmer 212. The database unit 222 may then transmit the EEG data records to the programmer 312 as necessary or desired.

Once a collection of EEG data having one or more instances of epileptiform activity has been placed in the programmer storage unit 312 for a specific patient, a template development module 322 can be run in combination with the EEG data display (FIG. 6, below) to annotate epileptiform activity records in the patient files and develop a patient specific seizure detection template. An EEG signal processor module 324 may be used to pre-process the EEG data to enhance its suitability for event detection; exemplary schemes for accomplishing this are described in Fischell and Harwood, U.S. patent application Ser. No. 09/556,415, referenced above.

The template development module 322 of the programmer 212 has, in particular, two capabilities: to analyze EEG records stored in the programmer storage unit 312 and identify preferred parameters using an optimization module 326, and to confirm the suitability of the preferred parameters on stored or new EEG records using a simulation module 328. The functions of the optimization module 326 and the simulation module 328 will be described in further detail below.

While certain of the functional components are illustrated in FIG. 3 as communicating with or through the operating system 320 and the GUI 316, it should be noted that depending on the implementation, as a matter of routine implementation choice, some, none, or all functional modules of the programmer 212 or its operating software program may operate in this manner.

Figure 4:
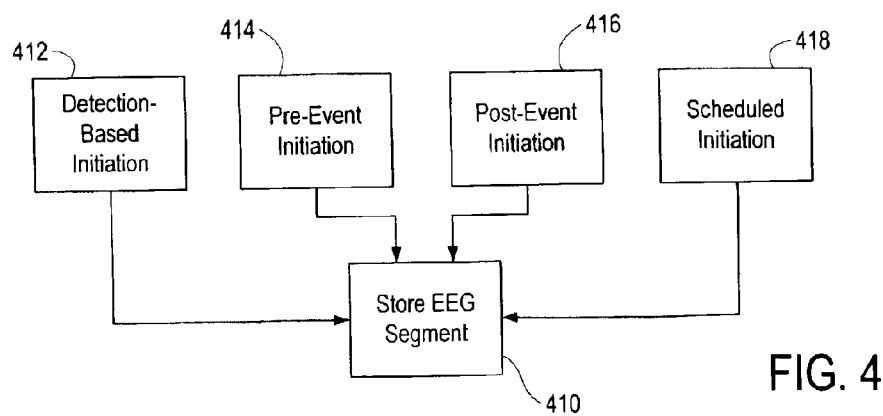
FIG. 4 is a flow chart showing a method for collecting patient EEG records with an implantable neurostimulator according to the invention.

FIG. 4 is a flow chart illustrating an embodiment of a method according to the invention for collecting patient EEG records. Within the present inventive method, the act of storing an EEG record in the neurostimulator memory (step 410) is initiated by an event that may include one of the following:

1. The event detection subsystem 122 and the CPU 128 (FIG. 1) detect a neurological event (step 412);
2. The patient detects an aura or some other sensation indicating a neurological event is imminent and transmits an "aura detected" command (step 414) to the implantable neurostimulator 110 (FIG. 1) from the patient's initiating device 224 (FIG. 2);
3. A clinical event (such as an epileptic seizure) occurs and the patient or caregiver sends an "event has occurred" command (step 416) to the neurostimulator 110 from the patient initiating device 224 or the programmer 212 (FIG. 2) or
4. The physician wishes to store baseline EEG records at pre-programmed or varying arbitrary times (step 418).

In each case, the implantable neurostimulator 110 of the implantable system will store in memory an EEG record for a time of X seconds before the event and Y seconds after the event. It should be noted that X and Y might vary for each case. For example, a command based on a seizure that has already occurred should not need much of a record after the event (i.e. Y=0 or small), but may prompt a longer X time than a command based on detection or prediction of the precursor, onset, or aura before a seizure. However, and preferably for simplicity of implementation, each type of event triggering storage of an EEG record may be caused to have the same pre-trigger recording time (X).

Accordingly, preferably, a system according to the invention will continuously buffer at least X seconds of EEG data, thereby allowing the previous X seconds to be saved when an event, as defined above and illustrated in FIG. 4, occurs.

In the disclosed embodiment of the invention, EEG records are stored by the neurostimulator 110 after they have been pre-processed by a sensing front end stage of the neurostimulator 110. Such pre-processing may include one or more stages of amplification, filtering, and other waveform processing (either in the analog or digital domain) intended to improve detection performance in a system according to the invention. In an alternative embodiment of the invention, EEG records are stored without any significant alteration or pre-processing, thereby allowing the programmer 212 to optimize pre-processing parameters, such as filter types and cutoff frequencies (and other filter parameters), amplifier gain settings, and the like. The use of EEG records that have not been pre-processed will be described in further detail below.

Figure 5:
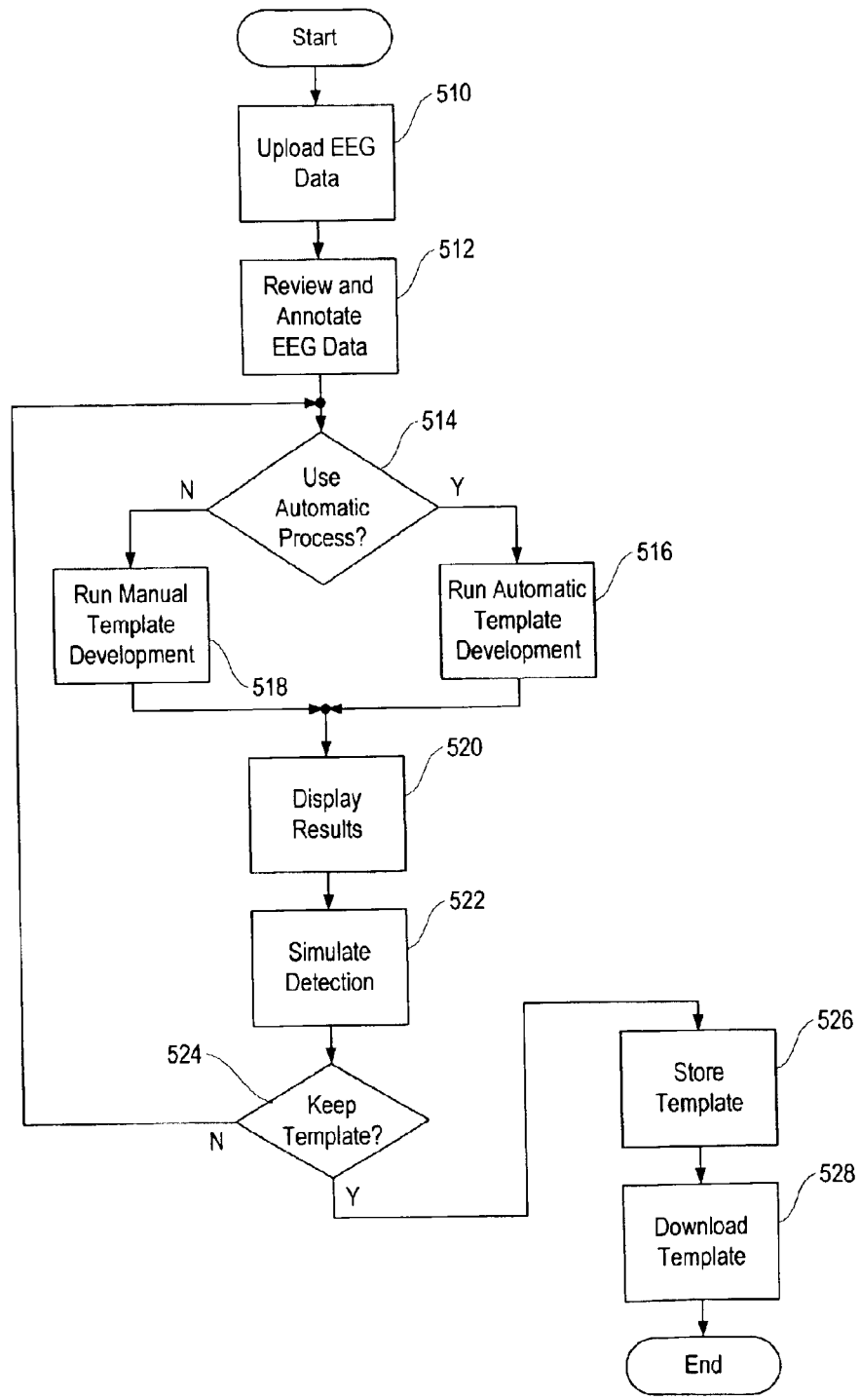
FIG. 5 is a flow chart illustrating a method according to the invention for transferring EEG records to a programmer and deriving a patient-specific template from the records.

The operations performed by a system according to the invention in uploading EEG records from the implantable neurostimulator 110 (FIG. 1) to the programmer 212 (FIG. 2), processing the records to develop an optimized event detection template, and downloading the event detection template back to the implantable neurostimulator 110 are illustrated in FIG. 5.

When appropriate (e.g., when commanded by the patient's initiating device 224 or the programmer 212, both illustrated in FIG. 2), the EEG data records will be uploaded (step 510) through the neurostimulator communications module 310 to the programmer 212. As described above, if not all necessary EEG records are stored within the implantable neurostimulator 110 or the programmer 212, the uploading process (step 510) may also cause additional available EEG records to be downloaded or otherwise retrieved from the database 222.

Using the programmer 212 in conjunction with its software operating program, the physician or EEG technician reviews all the EEG records, annotating actual seizures or other neurological events of interest (based on observation of the EEG signals or on clinical observation of the patient) (step 512). Once the events have been annotated, the software operating program is used to process the data, per the user's choice (step 514) either automatically (step 516) or manually (step 518) to develop a preferred event detection template for the patient. Manual template development is accomplished simply by providing an opportunity for the user to input parameter values. In an alternative embodiment of the invention, the manual template development process may be assisted with heuristic estimates or other automatically generated suggested parameter values. The automatic template development process will be described in further detail below and in connection with FIGS. 9, 12, and 14.

In one embodiment of the invention, it is possible to modify the EEG records to reflect electromagnetic noise conditions that may be experienced by the patient; such noise conditions may complicate event discrimination. As will be described in detail below with reference to FIG. 8, prior to performing either the automatic or the manual template development methods according to the invention (steps 516 and 518), it may be desirable to either add noisy baseline records to the set of EEG records being analyzed, or alternatively, to alter existing EEG records by superimposing stereotypical noise waveforms thereon. Performing these operations may cause the number of EEG records to be analyzed to proliferate significantly; however, the detection parameters obtained upon such EEG record modification are likely to be more robust and have an enhanced ability to discriminate between noise and other electrographic waveforms of interest, specifically the events sought to be detected.

After a template development process has been performed, the user is able to display the results (step 520). The results display can be presented to the user in any of several possible ways, such as a simple textual list of the parameters of the template or a graphical representation of the parameters. The user need not view the parameters, but a cursory review may serve as confirmation that the parameters chosen are within a reasonable range.

After displaying the results of the template development process (step 520), it is possible, in a preferred embodiment of the invention, to simulate the detection capability of the implantable neurostimulator 110 (step 522) by commanding the programmer 212 to perform the selected detection algorithm(s) on the EEG data records (either those records used to produce the template, a subset of those records, new data obtained from the implantable neurostimulator 110 or elsewhere, or a combination of the records used to produce the template and new data) and summarizing the results to the user. As described above, this simulation procedure may be performed with a template developed by the manual template development process (step 518) or the automatic template development process (step 516), or with detection parameters obtained elsewhere (e.g., uploaded from the implantable neurostimulator 110).

Once the results of either the manual or automatic template development process are displayed and simulated (steps 520–522), the physician can evaluate the results (in connection with criteria that will be described in detail below) and decide whether to keep the template (step 524). If not, either the automatic or manual template development process can be repeated. If the clinician does choose to keep the patient-specific event detection template generated as described herein, the template is stored (step 526) and downloaded to the implantable neurostimulator 110 (step 528) via the link 210 (FIG. 2).

While the operations illustrated in FIG. 5 are preferably performed largely by the programmer 212 (FIG. 2), it should be noted that, as described above, certain aspects of the invention allow EEG data records to be stored remotely in the database 222. Accordingly, it is possible for many of the data analysis operations performed by an embodiment of the invention to also be performed remotely on the data stored in the database, with essentially only the communications and programming capabilities resident in the programmer 212. The desired system architecture would be a matter of design choice, and aspects of both versions may be employed in a given embodiment. For example, if data has been uploaded directly to the database 222, it may be advantageous to perform a number of operations at the database level, while if data is uploaded to the programmer 212, it may be advantageous to have the programmer 212 perform the bulk of the processing specified by the invention.

A primary use for the centralized database 222 is to ensure that all EEG records necessary for an individual patient are available regardless of how many programmers uploaded the EEG records from the implantable neurostimulator 110. For example, a patient may spend time in two or more different geographic locations, and without the database 222, programmers at the multiple locations may each have an incomplete set of uploaded EEG records. However, if all EEG data is routinely uploaded from programmers to the database 222, then the database 222 can download all relevant EEG records to any given programmer, thereby providing the best selection of EEG records for determining detection parameters according to the invention. Alternatively, since all EEG data would available in the database 222, a patient's detection parameters may be found by using the database 222 directly instead of a programmer according to the invention.

Figure 6:
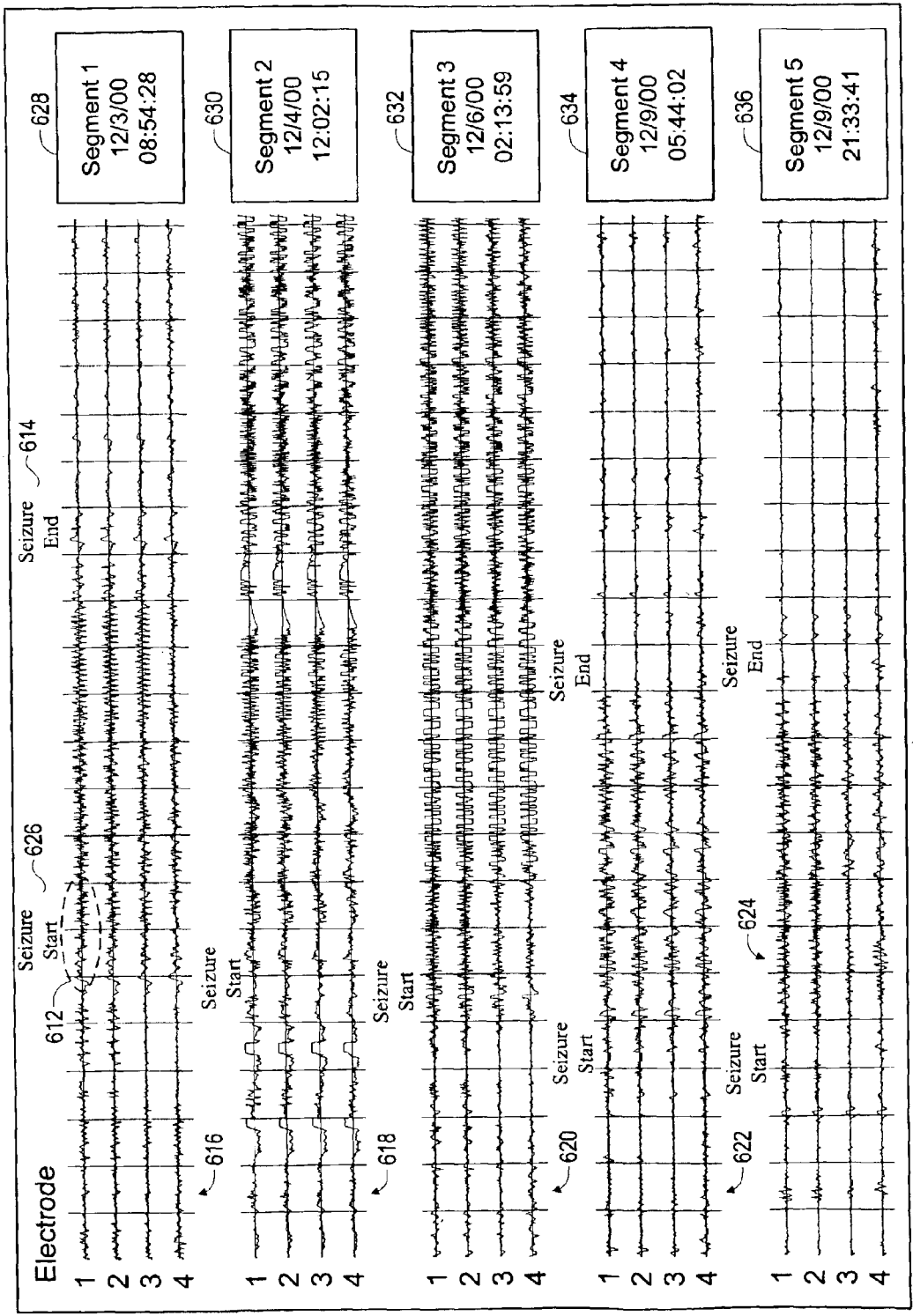
FIG. 6 is a multi-channel EEG screen showing five ninety-second EEG records containing epileptiform activity as recorded by an implantable neurostimulator and displayed by a programmer according to the invention.

Before either the automatic or manual template development processes (steps 516 and 518, FIG. 5) can be run, each EEG record containing seizure activity uploaded by the programmer 212 should be annotated to indicate the boundaries of the type of electrographic seizure activity sought to be detected. FIG. 6 represents an exemplary display screen 610 as it would appear after starts and ends of each seizure have been annotated using the software operating program. The screen 610 shows the inserted comment "Seizure Start" 612 located just before epileptiform activity appears on each of the EEG records 616 through 624, and the comment "Seizure End" 614 as epileptiform activity terminates. The end of seizure activity is visible only in records 616, 622, and 624, and not in records 618 and 620. It should be noted, however, that in a preferred embodiment of the invention the screen 610 (or each of the records 616–624) can be scrolled to allow the complete record to be viewed.

Each of the segments 616–624 bears a corresponding label 628–636 indicating the time and date at which the segment was recorded. This information may be useful to the reviewing clinician, and may indicate observable trends in event types or morphologies over time or at different times of day.

In an alternative embodiment of the invention, there is no need to annotate seizure ends. As will be discussed in further detail below, one important detection quality criterion is whether detection occurs near enough to an annotated seizure start. Accordingly, detection events that occur long after an annotated seizure start may not be generally indicative of a successful detection, and may in some cases increase the possibility of false positives. However, and preferably, it is possible to annotate seizure ends in the disclosed embodiment of the invention, and this is particularly important when stored EEG records contain both seizure activity and normal EEG activity (e.g., when an EEG record is appreciably longer than a seizure). This will enable enhanced discrimination by a system according to the invention between epileptiform EEG activity and baseline, or substantially normal, EEG activity.

In a presently preferred embodiment of the invention, it is also possible to annotate types of events other than seizures. For example, it may be possible to annotate one or more types of seizures, one or more different onset patterns, one or more different precursor patterns (for prediction), and sleep spindles (a normal EEG pattern observed only during sleep), to facilitate the detection of (or the avoidance of detection of, in the case of normal patterns such as sleep spindles) other EEG waveform patterns of interest, including noise. For the purposes of the disclosure herein, seizure annotation, detection, and optimization (and in particular, three specific algorithms for detecting seizures) are described in detail, but other electrographic patterns may be annotated, detected, and optimized in an analogous manner.

The seizure and other annotations according to the invention may be made initially by the clinician based on a visual review of EEG data, or may come indirectly from a patient's seizure log or other time-stamped record of clinical symptoms (such as a video seizure monitor). A seizure log stored on a PDA or other computing apparatus may be uploaded to the programmer 212 (or to the database 222) to provide rough or initial seizure annotations, which may then be adjusted as desired by the clinician.

To optimize epileptiform activity detection according to the present invention, the programmer user should also select at least one EEG channel or combination of EEG channels to use for epileptiform activity detection. In U.S. patent application Ser. No. 09/517,797, referenced above, Fischell and Harwood describe a method for selecting a single EEG channel or combination of EEG channels to use for epileptiform activity detection as a processed display channel (PDC). Fischell and Harwood also envision the use of multiple PDCs with detection based on logical operations between valid detections on each PDC.

Considering the EEG traces of FIG. 6, the choice of a single channel to use for template development may be readily apparent to a practitioner skilled in EEG analysis. Specifically, in the first EEG record 616, the first channel (indicated by the first label "1") shows an early onset 626 of epileptiform activity. In the illustrated example, and generally, the first channel in each segment contains data received from a single electrode or combination of electrodes, and appears to provide a relatively early indication of seizure activity in each illustrated segment. Accordingly, the first channel would be one acceptable choice as the channel to be analyzed by a system according to the invention.

Once all the identified electrographic seizures have been annotated in the existing stored EEG data records 616–624 (from the programmer storage unit 312, FIG. 3) as shown in FIG. 6, the seizure data is ready to be processed into an event data set. The event data set is defined as the patient-specific collection of EEG records comprising the multiplicity of annotated events, in the illustrated case seizures, for that patient. It should be noted that template development according to the invention is preferably an ongoing process, and as such, it is desirable to periodically increase the extent of the event data set upon the collection of additional data, thereby allowing "retraining." As input evaluation and annotation continues according to the invention, each stored EEG record for a patient is reviewed, and the events are annotated and added to the event data set. Data from unused channels can be discarded. When the last EEG data record has been thus processed, the process performed by the template development module 322 (FIG. 3) is started.

Once the event data set has been created, two different procedures are set forth below for producing a patient-specific detection template. These are the automatic and manual procedures illustrated in FIG. 5 (steps 516 and 518). One version of these techniques for use with long EEG files is disclosed in D. Fischell and J. Harwood, U.S. patent application Ser. No. 09/556,415, referenced above. However, the methods for producing patient-specific templates according to the invention described herein differ in several significant ways from the Fischell and Harwood methods. At the outset, the present invention differs from the previous Fischell and Harwood application by using only short EEG records such as those shown in FIG. 6, where some of the records are designated as baseline EEG activity.

Baseline activity includes those EEG records that do not represent any seizure or other ictal activity. It is envisioned that at least some of the baseline activity may be collected either by physician-initiated (or patient-initiated) requests for data recording transmitted to the implantable neurostimulator 110 (FIG. 1), by periodic recordings made by the implantable neurostimulator 110 at preset times or at arbitrary intervals, or as a result of false positive detections causing the storage of an EEG record. For examples of data collection strategies, see the description of FIG. 4 above.

Figure 7:
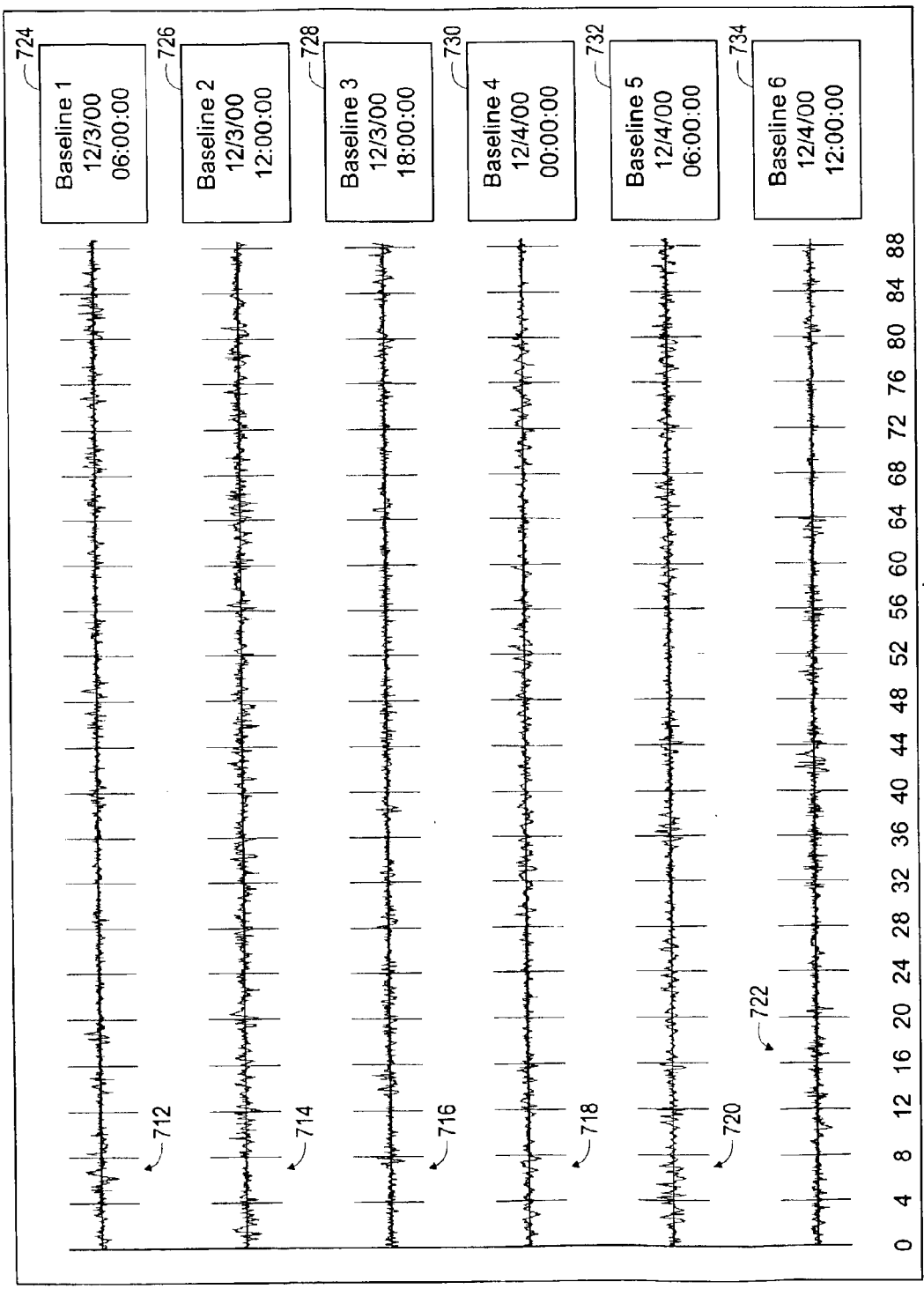
FIG. 7 shows stored EEG baseline records collected at preset times by an implantable neurostimulator according to the invention.

FIG. 7 shows an exemplary programmer display screen 710 showing six EEG records 712 through 722, labeled with corresponding labels 724 through 734, recorded at preset times by the implantable neurostimulator 110 and uploaded to the programmer 212 through the neurostimulator's data communication subsystem 130 (FIG. 1) and the programmer's neurostimulator communications module 310 (FIG. 3). There are no seizures to be annotated in this data, but it generally desirable to have the clinician review the records to look for any possible seizure-like activity missed by the event detection subsystem 122 (FIG. 1). Unlike FIG. 6, which shows EEG data from four electrodes for each recorded record, the baseline record recordings of FIG. 7 are for a single electrode channel each. This has the advantage of allowing four times the number of records to be stored in the same memory and is an important feature of the present invention. It is also envisioned that different electrodes could be used for each baseline record, or that under certain circumstances, all channels or a subset of the channels may be recorded, depending on desired aspects of the operating program of the implantable neurostimulator 110 (e.g., the particular triggers or times EEG records are being made).

It is also envisioned that baseline recordings could be initiated through specific or generic waveform detection templates that operate with or without the seizure detection templates developed according to the invention. These could be used to capture EEG records of interest to the treating physician such as sleep spindles or other unusual brain activity.

In a preferred embodiment of the invention, capturing baseline EEG records according to the scheme described above is not the most significant source of baseline data. Primarily, the implantable neurostimulator 110 (FIG. 1) is capable of transmitting multiple channels of sensed EEG signals to the programmer 212 (FIG. 2) in real time, enabling the capture of baseline records to be performed by the programmer 212 based on data constantly or intermittently being received from the neurostimulator 110. In this manner, the treating physician or other user has greater control over the signals that are captured and used as baseline, and contemporaneous clinical observations can be made to ensure that the patient is not experiencing a clinical seizure that is not clearly manifested in any of the channels being captured. The user should ensure that the signals captured are representative of a spectrum of possible baseline signals, including those from when the patient is asleep, awake, physically active, mentally concentrating, or in any other clinically relevant condition. Also, in an alternative embodiment, baseline records (and also event-containing records, such as those representing seizure onsets) can be retrieved from the database 222 or obtained from another source, such as a special-purpose EEG recording apparatus. If event-containing records are obtained in this manner, they should be annotated.

Figure 8:
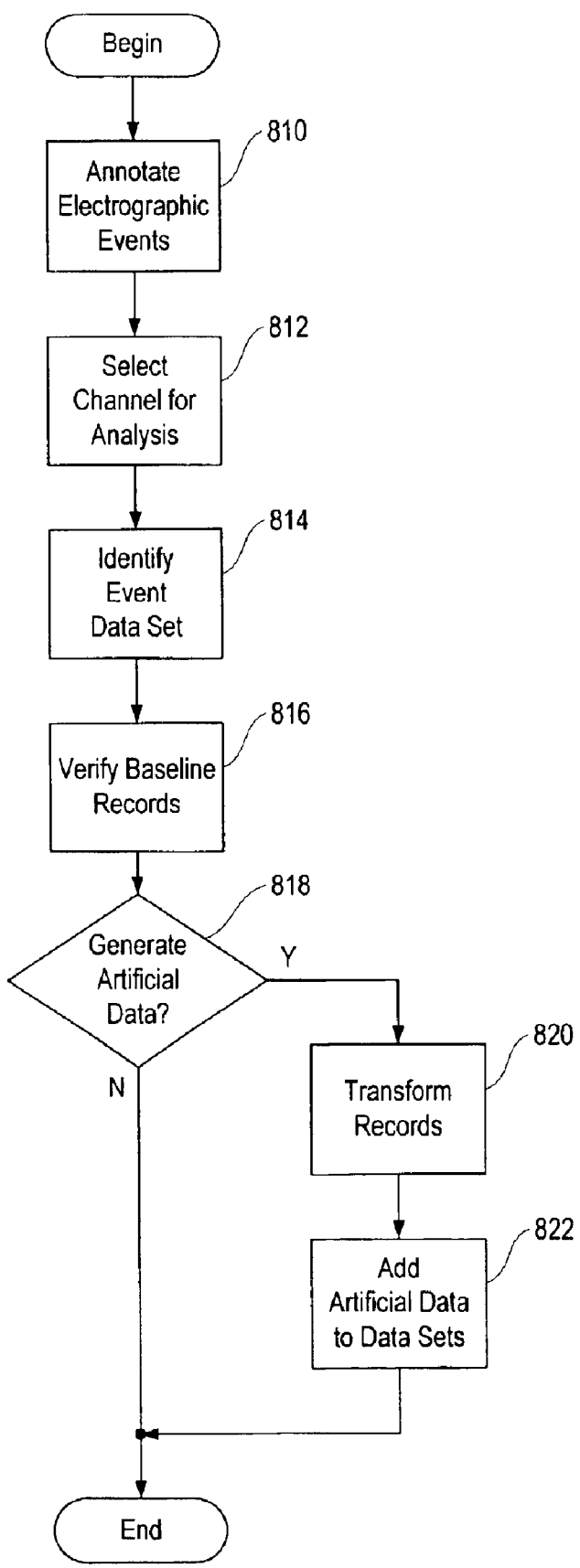
FIG. 8 is a flow chart illustrating the creation of a seizure data set according to the invention.

Referring now to FIG. 8, after all electrographic events have been annotated (step 810) and a channel has been selected for analysis (step 812), as illustrated in FIG. 6 and described above, and after the event data set has been identified (step 814) and sufficient baseline data has been collected and verified (step 816), as illustrated in FIG. 7 and described above, a system according to the invention is ready to produce a patient-specific event detection template.

Optionally, if the user chooses to generate artificial data (step 818), the programmer may generate additional data by transforming the seizure-containing (or other event-containing) and baseline records uploaded from the implanted neurostimulator or obtained elsewhere (step 820). In accordance with this embodiment of the invention, the EEG records corresponding to known seizures (as annotated by the clinician) can be slightly modified to make new data sets.

Useful modifications include varying the amplitude by up to about 20%, changing the "playback speed" by up to about 10%, adding a random in-band noise signal having an energy content of up to about 20% of the data set, or a combination of these and similar modifications. It should be noted that the variation percentages set forth above are guidelines only, and it may be advantageous in certain circumstances to have alternative settings. The result is a much larger dataset (including both event-containing and baseline records) that facilitates generation of a set of detection parameters that maintains high sensitivity, but is possibly more specific than a set of detection parameters generated from the one or few real seizures recorded. Typically, manual annotations need not be made to artificial data generated as described above, as previous annotations in the original (untransformed) records will generally correspond to the desired annotation points in the artificial data records, and a system according to the invention would be capable of applying the existing annotations to the newly generated artificial data records.

As described above, environmental noise is a confounding signal that may adversely affect the performance of a neurological event detector according to the invention. Rather than wait for the patient to experience noise, it is anticipated that stereotypical noise records may be included in the training set of data to arrive at detection parameters that are capable of discriminating noise from neurological events. Typical sources of electrographic noise include cellular telephones, fluorescent and other gas discharge lighting, welders, electric motors, RF amplifiers, electronic theft detectors, and AC power lines. Stored noise-containing electrographic records generated in controlled environments, or recorded by a different patient, may be added to a patient's data set of stored EEGs to improve the detection parameters, or simulated noise signals may be superimposed onto the patient's stored EEG records (both event-containing and baseline). As with the artificial data described above, the addition of noise typically will not affect existing annotations, and a system according to the invention is capable of transferring annotations into new records containing noise superimposed upon real EEG data.

Once any desired artificial data records have been generated as described above, they are added to the existing event-containing and baseline data sets (step 822), and the template generation process described herein operates on the artificial data records in conjunction with the original data records with no distinction between the two.

The automatic process for producing a patient-specific event detection template (step 516, FIG. 5) according to the invention is described in detail with reference to FIG. 9. As described in U.S. patent application Ser. No. 09/896,092, referenced above, a responsive neurostimulator according to the invention is capable of using three different analysis tools in various combinations, namely a half wave analysis tool, a line length analysis tool, and an area analysis tool.

A neurostimulator system according to the invention receives EEG data, pre-processes it, digitizes it, and stores it in segments as generally described above. Each of the analysis tools described below operates on records of digitized EEG data recorded by the implantable neurostimulator 110 (or obtained from some other source, such as a special-purpose EEG recorder) that have been uploaded to the programmer 212.

The half wave analysis tool measures characteristics of an EEG signal related to the signal's frequency and amplitude components. In general terms, a half wave is an interval between a local waveform minimum and a local waveform maximum; each time a signal "changes directions" (from increasing to decreasing, or vice versa), with an allowance for a programmable hysteresis value (and subject to limitations that will be set forth in further detail below), a new half wave is identified.

The identification of half waves having specific amplitude and duration criteria allows some frequency-driven characteristics of the EEG signal to be considered and analyzed without the need for computationally intensive transformations of normally time-domain EEG signals into the frequency domain. Specifically, the half wave feature extraction capability of the invention identifies those half waves in the input signal having a duration that exceeds a minimum duration criterion and an amplitude that exceeds a minimum amplitude criterion. The number of half waves in a time window meeting those criteria is somewhat representative of the amount of energy in a waveform at a frequency below the frequency corresponding to the minimum duration criterion. And the number of half waves in a time window is constrained somewhat by the duration of each half wave (i.e., if the half waves in a time window have particularly long durations, relatively fewer of them will fit into the time window), that number is highest when a dominant waveform frequency most closely matches the frequency corresponding to the minimum duration criterion.

Accordingly, the number of qualified half waves (i.e., half waves meeting both the duration criterion and the amplitude criterion) within a limited time period is a quantity of interest, as it may be representative of neurological events manifested in the corresponding frequency range corresponding to the half wave criteria.

It should be observed that signal processing according to the invention, in both the implantable neurostimulator 110 (FIG. 1) and in the programmer 212 (FIG. 2), is generally performed on the basis of "processing windows," which are discrete consecutive segments of EEG data, preferably 128 or 256 milliseconds in length. Although detection performed by the implantable neurostimulator 110 must be accomplished in real time, no such limitation exists for the programmer 212 when performing the template development operations performed herein. Whether analysis is performed in real time or not, at the end of each processing window, EEG data in that-processing window is analyzed as described herein. This is primarily done to allow processing to be performed by the implantable neurostimulator 110 on an interrupt-driven basis, so that the CPU 128 is active only when there is EEG data to be analyzed; the programmer 212 operates similarly to ensure that template development and simulation results will correspond closely to what the implantable neurostimulator 110 is able to achieve.

In the illustrated embodiment of the invention, there are two levels of half wave analysis. For the first level, five parameters are available to select the waveform template parameters, i.e. the parameters that specify what types of half waves the detector in the implantable neurostimulator 110 and the programmer 212 will identify. In the disclosed embodiment of the invention, the available waveform template parameters for the half wave detector algorithm are minimum peak-to-peak amplitude (in arbitrary), minimum wave duration (in milliseconds), hysteresis value, the desired number of half waves, and the total duration (in milliseconds). At the end of each processing window, half waves meeting the minimum peak-to-peak amplitude and minimum half wave duration criteria are identified and queued. If there have been at least the desired number of half waves in the preceding total duration, then the half wave analysis tool indicates that the current processing window contains a successful first-level detection.

For the second level of analysis, two parameters are available to further select the combinations of half wave characteristics within an EEG record that will lead to a detection. Those parameters are an analysis window size (in terms of processing windows) and an analysis window count. These parameters implement an "X of Y criterion," which in effect measures the density of first-level detections. Specifically, a second-level detection is made if and only if there are at least a certain number of processing windows containing first-level detections ("X," the analysis window count) in the prior period of processing windows ("Y," the analysis window size).

Consequently, second-level detections can be made once every processing window, but generally reflect information obtained from one or more additional previous processing windows (as in a "sliding window" scheme). In accordance with the invention, second-level half wave detections may be selectively inverted (so that a failure to have the criteria met causes a detection to be made, instead of the default, which is for a detection to be made when the criteria are met), and may have persistence applied (so that a single detection has a continuing effect for one or more processing windows in the future). Inversion and persistence are described in greater detail in U.S. patent application Ser. No. 09/896,092, referenced above.

The line length analysis tool is a simplification of waveform fractal dimension, allowing a consideration of how much variation an EEG signal undergoes. Accordingly, the line length analysis tool according to the invention enables the calculation of a "line length" for an EEG signal within a time window. Specifically, the line length of a digital signal represents an accumulation of the sample-to-sample amplitude variation in the EEG signal within a time window.

Stated another way, the line length is representative of the variability of the input signal. A constant input signal will have a line length approaching zero (representative of substantially no variation in the signal amplitude), while an input signal that oscillates between extrema from sample to sample will approach the maximum line length. It should be noted that while "line length" has a mathematical-world analogue in measuring the vector distance traveled in a graph of the input signal, the concept of line length as treated herein disregards the horizontal (X) axis in such a situation. The horizontal axis herein is representative of time in arbitrary units, and in the disclosed embodiment of the invention has no bearing on the calculation of line length.

The line length analysis tool according to the invention has a single level of analysis. Six parameters are available: line length window size (in multiples of the processing window size), line length threshold type (percentage or fixed offset), line length threshold value (depending on the type), line length trend sample count, line length trend window size (in multiples of the processing window size), and line length trend sample interval (in large multiples of the processing window size). In an alternative embodiment of the invention, also present (and available to be optimized upon) are one or more parameters representative of a desired non-linear transformation to be performed on each sample value before the accumulated line length is calculated. For example, it may be advantageous in certain circumstances to calculate the difference between adjacent samples using the squares of the sample values, or to calculate the square of the difference between sample values, or both. It is contemplated that other transformations (such as square root, exponentiation, logarithm, and other nonlinear functions) might also be advantageous in certain circumstances.

At the end of each processing window, accumulated line length is added to a running line length total representing the line length of a window having a duration equal to the line length window size, and the average line length is calculated as the average of these summed values. This running line length average is compared to a threshold obtained from a line length trend. If the line length threshold type is a percentage, then the average is divided by the trend (and scaled into percentage units) and compared to the threshold (which can be either above or below 100%). If the line length threshold type is a fixed offset, then the trend is subtracted from the average, and the result is compared to the threshold (which can be either positive or negative).

The line length trend is calculated as a relatively long-term average of observed line lengths. The trend is recalculated regularly and periodically, after each recurring line length trend sample interval passes. Each time the line length trend interval passes, the line length trend is calculated or updated. In a presently preferred embodiment of the invention, this is accomplished by calculating an average of several (the line length trend sample count) trend samples, each of which represents the average of a number (the line length trend window size) of consecutive processing windows of line lengths.

At the end of each processing window, the difference (fixed offset threshold) or ratio (percentage threshold) of the average line length (described above) and the line length trend is compared to the appropriate fixed offset or percentage threshold (also described above), and if the total exceeds the threshold, a successful line length detection has been made. As with the half wave analysis tool, line length detections can be made once every processing window, but generally reflect information obtained from one or more additional previous processing windows (as in a "sliding window" scheme). In accordance with the invention, line length detections may be selectively inverted (so that a failure to have the criteria met causes a detection to be made, instead of the default), and may have persistence applied (SQ that a single detection has a continuing effect for one or more processing windows in the future).

The area analysis tool is a simplification of waveform energy. Accordingly, the area analysis tool according to the invention enables the calculation of the area under the EEG waveform curve within a time window. Specifically, the area is calculated as an aggregation of the EEG's signal total deviation from zero over the time window, whether positive or negative. The mathematical-world analogue for area is the mathematical integral of the absolute value of the EEG function (as both positive and negative signals contribute to positive energy). Once again, the horizontal axis (time in arbitrary units) makes no contribution to the area under the curve as treated herein. Accordingly, an input signal that remains around zero will have a small area, while an input signal that remains around the most-positive or most-negative values (or oscillates between those values) will have a high area.

The area analysis tool according to the invention has a single level of analysis. Six parameters are available (they are essentially equivalent to the parameters used by the line length analysis tool): area window size (in multiples of the processing window size), area threshold type (percentage or fixed offset), area threshold value (depending on the type), area trend sample count, area trend window size (in multiples of the processing window size), and area trend sample interval (in large multiples of the processing window size). In an alternative embodiment of the invention, also present (and available to be optimized upon) are one or more parameters representative of a desired non-linear transformation to be performed on each sample value before the accumulated area is calculated. For example, it may be advantageous in certain circumstances to calculate the square of the current sample rather than its absolute value. The result of such a transformation by squaring each sample will generally be more representative of signal energy, though it is contemplated that other transformations (such as square root, exponentiation, logarithm, and other nonlinear functions) might also be advantageous in certain circumstances.

At the end of each processing window, accumulated area is added to a running area total representing the area of a window having a duration equal to the area window size, and the average area is calculated as the average of these summed values. This running area average is compared to a threshold obtained from an area trend. If the area threshold type is a percentage, then the average is divided by the trend (and scaled into percentage units) and compared to the threshold (which can be either above or below 100%). If the area threshold type is a fixed offset, then the trend is subtracted from the average, and the result is compared to the threshold (which can be either positive or negative).

The area trend is calculated as a relatively long-term average of observed areas. The trend is recalculated regularly and periodically, after each recurring area trend sample interval passes. Each time the area trend interval passes, the area trend is calculated or updated. In a presently preferred embodiment of the invention, this is accomplished by calculating an average of several (the area trend sample count) trend samples, each of which represents the average of a number (the area trend window size) of consecutive processing windows of areas.

At the end of each processing window, the difference (fixed offset threshold) or ratio (percentage threshold) of the average area (described above) and the area trend is compared to the appropriate fixed offset or percentage threshold (also described above), and if the total exceeds the threshold, a successful area detection has been made. As with the half wave and line length analysis tools, area detections can be made once every processing window, but generally reflect information obtained from one or more additional previous processing windows (as in a "sliding window" scheme). In accordance with the invention, area detections may be selectively inverted (so that a failure to have the criteria met causes a detection to be made, instead of the default), and may have persistence applied (so that a single detection has a continuing effect for one or more processing windows in the future).

Where a detector threshold is based upon trends, contexts, or other dynamic attributes of EEG signals, there are several possibilities for ensuring that such attributes are preserved in EEG records for use by a programmer 212 (FIG. 2) according to the invention. Preferably, to avoid the need to store further information with EEG records, any trends used in connection with the invention (in an implantable device or a programmer 212) should be short enough to allow trends to fully develop in the portion of a stored EEG record that occurs before an event sought to be detected; a sufficient amount of pre-trigger information should be captured to enable this. Alternatively, raw or calculated window-based trend data may be stored in connection with each EEG record, thereby allowing the programmer 212 to access such data even in the context of isolated EEG records. It may also be possible to truncate, sub-sample, or simulate trends using baseline data to predict what a trend may be. There are other possibilities that will be apparent upon consideration.

The optimization of the above-described analysis tool parameters will be described with reference to the search strategy illustrated in FIG. 9, referred to herein as a "greedy line search" (a type of univariate method of multidimensional optimization described in Brooks S., "A discussion of random methods for seeking maxima" *Operations Research* 1958; 6(2):244–51). In a presently contemplated embodiment of the invention, each of the analysis tools described above is optimized independently and separately, without consideration of detection persistence (although it is possible, and in some circumstances might be desirable, to consider persistence at the same time). The parameters for each analysis tool are then combined into an overall parameter set accounting for all three analysis tools by optimizing them together (e.g., performing a greedy line search on all tools simultaneously, using each tool's detection persistence as the variable parameters in the search). Finally, the preferred subset of detection tools is identified by testing the performance of all tool subsets exhaustively. This combination process will be described in detail below with reference to FIG. 20. Alternatively, all of the parameters for all of the analysis tools, including persistence and inversion, may be treated as a single large parameter set, upon which the method of FIG. 9 may operate.

Figure 9:
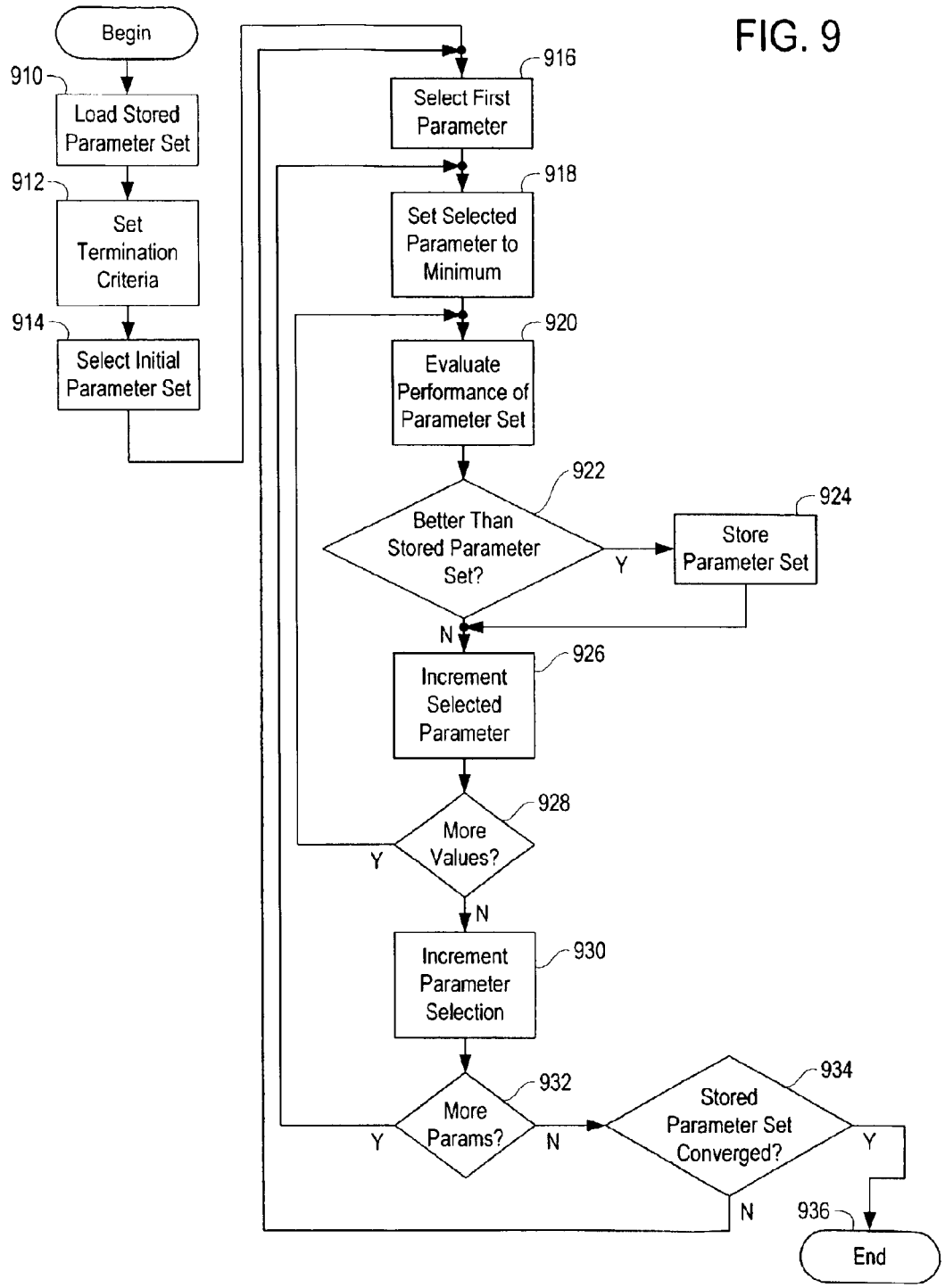
FIG. 9 is a flow chart illustrating the greedy line search automated template development process used with EEG records captured by an implantable neurostimulator according to the invention.

Furthermore, if there are multiple types of events to be optimized upon (e.g., multiple types of seizures, multiple types of onsets, etc.), each type of event calls for a separate and independent parameter set, and the procedure illustrated in FIG. 9 should be performed once for each event type. The implantable neurostimulator 110 has multiple parallel sets of analysis tools, and one set of analysis tools can be used for each desired event type.

The process of FIG. 9 begins by loading the stored parameter set (step 910) with values that are to be optimized. Criteria for determining whether a parameter set is "optimized," and specifically several components that are combined into a performance metric, are described below in connection with FIGS. 10–11 and elsewhere. The stored parameter set generally takes the form of a data structure that ultimately can be downloaded to and used by the implantable neurostimulator 110, though it should be noted that a translation step can alternatively be performed later to convert the stored parameter set into data recognizable by the neurostimulator 110. The user, typically a clinician, has an opportunity to set termination criteria (step 912), to specify how well a parameter set must perform (or how well-converged it must be) before the method of FIG. 9 may terminate (e.g., one or more convergence bounds or a limit on permitted iterations). The user may also select various weights for the various components of the performance metric at this stage.

An initial parameter set is then selected (step 914). Initial values for each parameter may be taken from the loaded parameter set (step 910) or heuristically calculated or pre-programmed default parameters expected to produce advantageous results. For example, where no loaded parameter set is available, for some parameters, such as minimum peak-to-peak voltage, minimum wave duration, and others, initial parameters may be derived by heuristic analysis of annotated event records—e.g., slightly more than the average wave characteristics during annotated seizures. For other parameters, such as half wave analysis window size, line length window size, and others, initial parameters may be derived from pre-programmed values as above—e.g., a line length window size of thirty-two processing windows may be a useful starting point. Alternatively, all parameters may be initially selected from pre-programmed defaults.

The first parameter in the parameter set is then selected (step 916); this parameter will be varied in subsequent steps to determine its best value. The selected parameter is set to its minimum value (step 918). The performance of the modified parameter set is then evaluated (step 920) according to a performance metric based on criteria that will be described in further detail below (with reference to FIGS. 10–11). If the performance of the modified parameter set is better than the previously stored parameter set (step 922), then the modified parameter set is stored (step 924). The selected parameter is then incremented (step 926). If there are more values to consider (step 928), the new parameter set is evaluated (step 920) and the process repeats. If the parameter has reached the end of its permissible range and there are no more values to consider (step 928), the parameter selection is incremented (step 930), thereby choosing the next parameter in the parameter set, and as long as there are more parameters to modify (step 932), the newly selected parameter is set to its minimum (step 918), and that parameter is tested over its range of values along with the other parameters in the stored parameter set.

If there are no more parameters to consider (step 932), the stored parameter set is compared to the parameter set stored after the prior iteration (or at the outset, step 910, if only one pass through the method has been completed). If the stored parameter set has converged sufficiently (step 934) according to the termination criteria set by the user in step 912, then the process ends (step 936), and the most recent stored parameter set is used in the patient-specific detection template. Otherwise, if the process is not able to end, the first parameter is again selected (step 916), and the iterative-process repeats until convergence is achieved or until a pre-defined or programmed number of iterations have been performed (which may indicate that no solution is possible given the specified initial parameter set and termination criteria). It should also be noted that testing for convergence (step 934) can be performed at other times during the process illustrated in FIG. 9, for example after each "line" in the greedy line search is completed and all values for a parameter have been tested (between steps 928 and 930).

The search strategy illustrated in FIG. 9 and described above is considered a "greedy line search," in that it varies only one parameter at a time (therefore testing along a line in multidimensional parameter space), cycling through values (i.e., points along a line) and then parameters (i.e., lines in different dimensions) one at a time until a preferred parameter combination is found. It should be noted that there may be more than one "solution" (i.e., optimum parameter combination) in the multidimensional parameter space, and that the greedy line search may converge to a locally preferred parameter combination that does not perform as well as other untested combinations in parameter space. However, these potential disadvantages are far outweighed by the computational resources that would be necessary to perform an exhaustive brute-force search on the parameter space with the resolution required by a system according to the invention. Such an exhaustive approach would be impractical, and even with current computing technology, may take many years to complete. To give but one example using the half wave analysis tool, if the threshold number of waves is set to cover a range of 4 through 10 in intervals of one, the minimum wave duration is set to cover 30 ms through 50 ms in intervals of one millisecond, the peak-to-peak voltage is set to cover 150 µV through 250 µV in intervals of 1 µV, and the total duration is set to range from 500 ms to 2,000 ms in intervals of 10 ms, and further if the analysis window size is set to range from 3 to 6 in intervals of one, and the analysis window count is set to range from 2 to 4 in intervals of one, the total number of parameter combinations will be 7×21×101×151×4×3, or approximately 26.9 million. In a clinically advantageous context with finer resolution, incorporating hysteresis and other variables, the number of combinations to test may be even greater than that. In contrast, the number of parameter combinations required per iteration of this example using a greedy line search algorithm (as described in FIG. 9) would be 7+21+101+151+4+3, or 287. Typically, the iteration limit is set to four, so the maximum number of parameter combinations would be 287×4, or 1,148.

Figure 10:
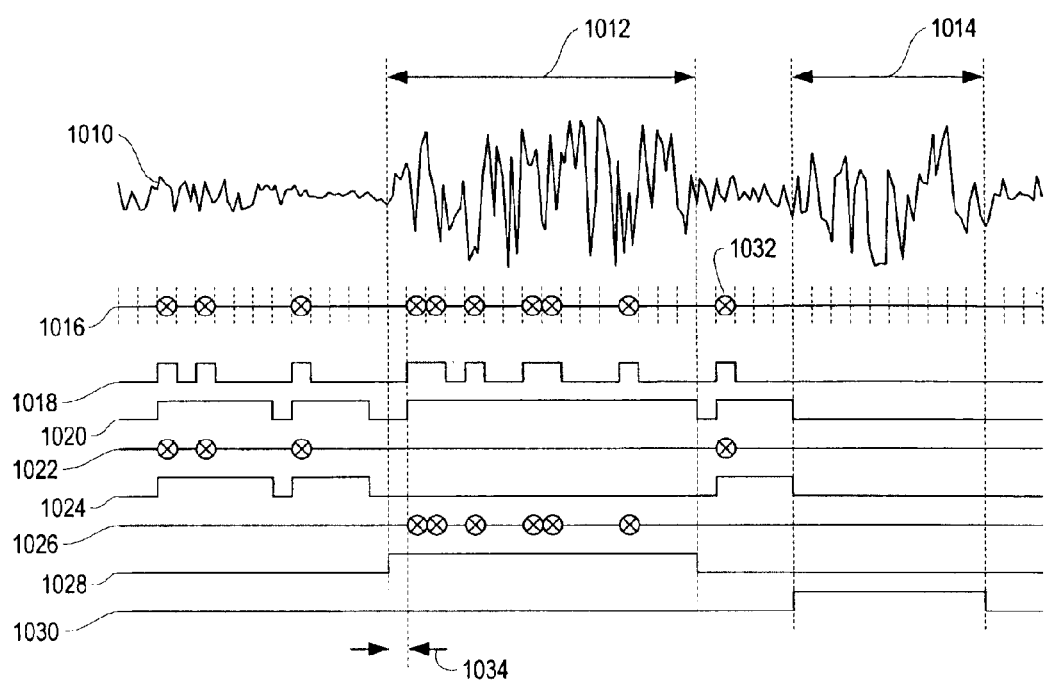
FIG. 10 illustrates an exemplary EEG waveform and a set of correct and false event detections according to the invention.

In connection with FIG. 10, it is useful to consider the various types of correct and incorrect detections (and failures to detect) possible in a system according to the invention and advantageous in calculating an overall performance metric as set forth above. An exemplary EEG trace 1010 includes two regions of seizure activity—a first seizure region 1012 and a second seizure region 1014. The two seizure regions are annotated as such by a user of a system according to the invention, as described above in connection with FIG. 6. It should be noted that the exemplary EEG trace 110 of FIG. 10 is fabricated and simplified; its characteristics are visually apparent for purposes of explanation herein, and the seizure regions 1012 and 1014 but its characteristics may or may not have any real-world seizure detection significance.

In general, two types of detection errors are possible: false positives (detection made outside of an annotated event) and false negatives (no detection made within an annotated event). Analogously, two types of correct detections are possible: correct positives (detection made within an annotated event) and correct negatives (no detection made outside of an annotated event). These four detection permutations can be considered on both a point basis (one processing window at a time) or on a block basis (where multiple detections within an annotated event or multiple detections in processing windows in close proximity to each other are treated as a single block).

Accordingly, there are eight total detection permutations: point false positives, point false negatives, point correct positives, point correct negatives, block false positives, block false negatives, block correct positives, and block correct negatives. A combination of four of these is considered to provide especially useful information in the context of a performance metric according to the invention.

An exemplary first string of detections 1016 is illustrated in FIG. 10. Each of the circles in the first string of detections 1016 represents a point detection corresponding to a processing window (processing window boundaries are indicated by vertical hash marks). As described above, detections are generally made only once per processing window. Some of the point detections occur within the annotated seizure regions 1012 and 1014, while others do not.

A first logic signal trace 1018 represents a detector output signal corresponding to the detections 1016. A logical true signal is output when a detection is made (indicating a positive detection); a logical false is output otherwise (indicating no detection).

A second logic signal trace 1020 represents the first logic signal trace 1018 with persistence applied. Persistence is set to three processing windows; in the illustrated example, each detection persists for three processing windows beyond the time it was triggered. Persistence is preferably a programmable parameter that can be set to any of a range of values.

A second string of detections 1022 represents point false positive detections, i.e., those detections 1016 that are outside of the annotated seizure regions 1012 and 1014.

A third logic signal trace 1024 represents block false positive detections, i.e., those detections including persistence 1020 that fall outside of the annotated seizure regions 1012 and 1014. Persistence is used to merge point false positive detections into block false positive detections, because unlike the annotated events (such as the seizure regions 1012 and 1014), there is not necessarily any common characteristic, other than adjacency in time, that would cause point false positive detections to be grouped together.

It should be noted that alternative definitions of "block" are possible and usable in the context of the present invention. For example, an entire EEG record might be regarded as a block. Alternatively, blocks may be defined as groups of point detections merged in accordance with a clustering algorithm or a probability density; suitable algorithms are well known.

A third string of detections 1026 represents point correct positive detections, i.e., those detections 1016 that are within the annotated seizure regions 1012 and 1014. Note that there are no point correct positives within the second annotated seizure region 1014.

A fourth logic signal trace 1028 represents block correct positives; it is set to logical true for the duration of an annotated seizure region if a point correct positive detection is made during the region. Accordingly, this signal trace 1028 is true (high) for the first annotated seizure region 1012, but not for the second annotated seizure region 1014.

A fifth logic signal trace 1030 represents block false negatives; it is set to logical true for the duration of an annotated seizure region if no point correct positive detection is made during the region. Within annotated regions, the block false negative signal trace 1030 is the logical inverse of the block correct positive signal trace 1028. Accordingly, this signal trace 1030 is true (high) for the second annotated seizure region 1014, but not for the first annotated seizure region 1012.

Latency is another detection characteristic that is important in the context of the current invention. The time interval between the annotated beginning of an event and the first point correct positive (represented in FIG. 10 by an interval 1034) represents a time delay from the electrographic beginning of an event and when the event would be detected by a system according to the invention. Clearly, the shortest possible detection latency is desired, allowing the implantable neurostimulator 110 (FIG. 1) to be able to apply responsive therapy or take other action at the earliest possible time.

It is possible, when a false positive detection is made before the beginning of an annotated event, to advantageously reclassify such a false positive as a correct positive if it is likely to be predictive of the annotated event. For example, a detection 1032 occurs shortly before the second annotated seizure region, and may be considered, in an embodiment of the invention, to be a correct positive with a negative detection latency rather than a false positive. The use of such a pre-annotation positive detection with negative latency to achieve prediction is described in further detail below.

The foregoing identified detection permutations, namely point and block false positives, point and block correct positives, block false negatives, and detection latency, have been found to be useful in calculating a combined performance metric according to the invention. The other permutations, specifically point and block false negatives and point false negatives, are not used in the performance metric disclosed herein.

Figure 11:
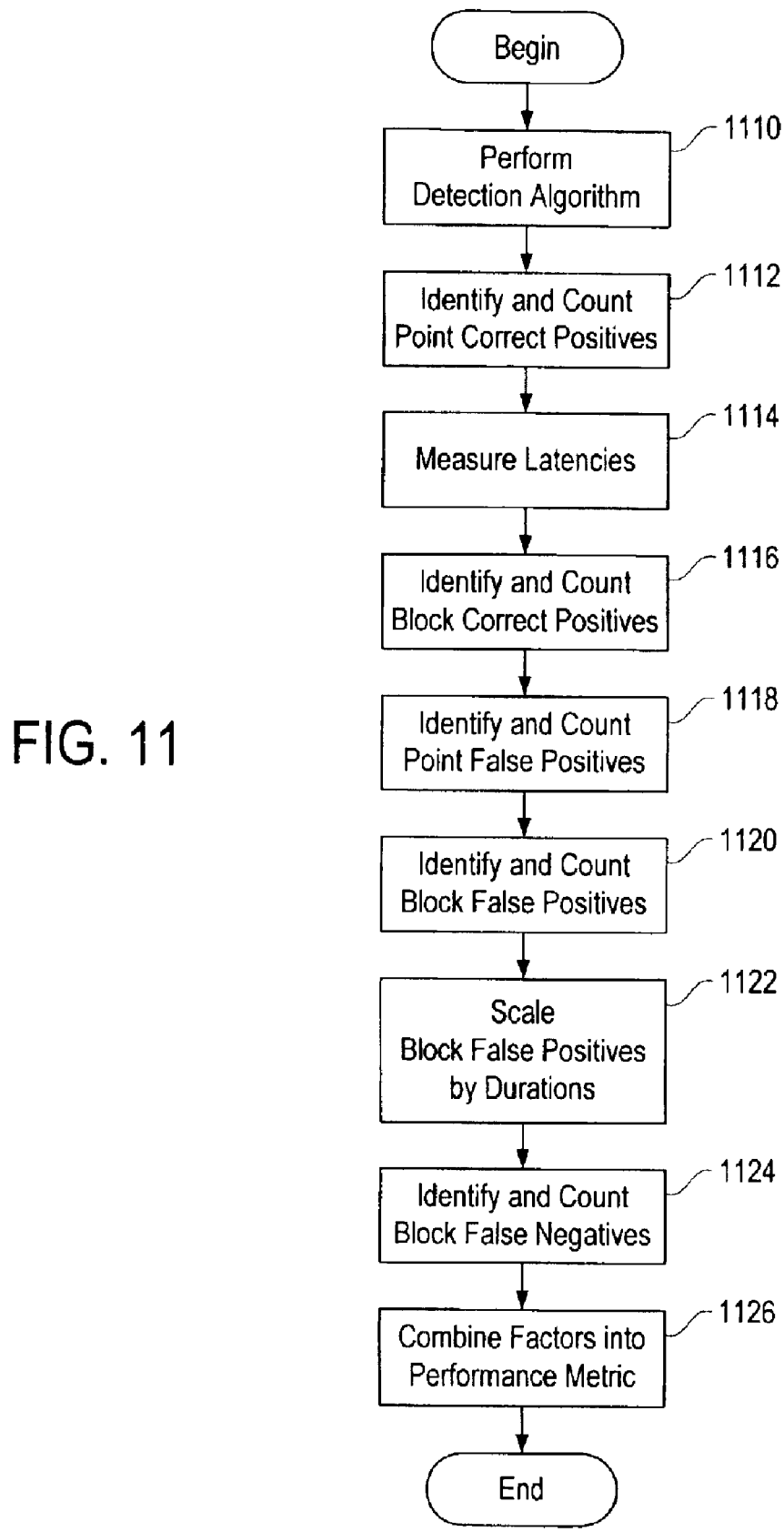
FIG. 11 is a flow chart illustrating the computation of a detector performance metric for use by a programmer according to the invention.

The combination of the above-described factors into a performance metric (otherwise known as an objective function or utility function), as performed by a system according to the invention, is illustrated by the flow chart of FIG. 11. Initially, and as specified by step 920 of the automatic template development process (FIG. 9), the detection algorithm specified by the analysis tool (or tools) being optimized is performed on all data, including the event data set and baseline EEG data (step 1110). Point correct positives are identified and counted (step 1112). Detection latencies are measured (step 1114) based on the point correct positives and the annotated events.

Block correct positives are identified and counted (step 1116), as are point false positives (step 1118) and block false positives (step 1120). Block false positives, as described above, are identified by using detection tool persistence to merge point false positives into blocks. Accordingly, the durations of any block false positives identified are used to scale the count (step 1122). Finally, block false negatives are identified and counted (step 1124).

It should be noted that in a preferred embodiment of the invention, certain modifications to the raw counts described above may provide advantageous results. For example, as illustrated in FIG. 10, described above, a point positive detection 1032 occurring shortly before the beginning of an annotated event (e.g., before a "Seizure Start" annotation 612, FIG. 6) may not represent a false positive, even though it occurs outside of the annotated event. It may instead be a predictive detection, identifying a significant characteristic of the EEG signal that might not have been apparent to the practitioner who annotated the beginning of the event. Accordingly, point positive detections occurring a limited amount of time (either a programmable or preset amount of time) before an event should be considered correct positives and not false positives. Similarly, because the detection latency (the amount of time between the start of an annotated event and such a pre-annotation correct positive, as that quantity is measured according to the invention) will be measured as a negative quantity, certain negative detection latencies should be considered advantageous and treated accordingly. Observe, however, that highly negative detection latencies are more likely representative of false positive detections.

Similarly, positive detections occurring shortly after the end of an annotated event should preferably be disregarded. As with the pre-annotation detections described above, such post-annotation detections may represent waveform characteristics not observed by the clinician when the events were annotated. Moreover, if the actual annotated event has also been correctly detected and identified (and particularly if the event is an onset or seizure), it is likely that in practice the implantable neurostimulator 110 will apply responsive therapy, altering the nature of the waveforms that are likely to follow. Generally, detection will be disabled during and shortly after responsive therapy according to the invention.

The foregoing individual performance factors, identified, counted, measured, and scaled as set forth above, are then combined into an overall performance metric (step 1126) used by the automatic template development process (FIG. 9). In a presently preferred embodiment of the invention, each of the factors is given a numeric weight (which may be selected as part of the termination criteria set in step 912, FIG. 9, or may be pre-programmed), and the factors, scaled by their corresponding numeric weights, are added together to form a scalar performance metric. Preferably, and consistent with the disclosed embodiment of the invention, an increasing scalar value of the performance metric indicates poorer performance; better values are lower. In an alternative embodiment, the factors are collected as the terms of a multidimensional performance vector, which can be compared to other performance vectors by any of numerous known vector distance metrics.

The automatic template development methods described above are characterized as generally being operative on a single detection algorithm or tool (e.g., half wave, line length, or area) at a time. It is considered advantageous, however, to be able to configure the implantable neurostimulator 110 so that multiple detection tools are used to detect a single event. Accordingly, several strategies are possible for developing a detection template that includes parameters for multiple detection tools.

It is presently considered preferable to perform template development on each detection tool as described above separately (or twice for each tool, to accommodate selective inversion usable in combining the results of the tools), and then to combine the results via Boolean logic. For example, the implantable neurostimulator 110 may be programmed to detect a specified event only if the half wave, line length, and area tools all individually indicate (over a short period of time specified by the persistence parameter) that a detection should be made. In this embodiment of the invention, the combination of detection tools may also be optimized upon in a subsequent process, modifying persistence for each of the applicable tools according to the greedy line search described above. This would then be followed by an exhaustive search of the various combinations of tools, identifying the subset that provides the best performance.

Other combinations of the detection tools or algorithms may also be used. However, note that a Boolean AND combination of multiple detection algorithms will generally result in an output that is more conservative (i.e., less likely to detect an event) than each individual detector used alone, and may have long detection latencies. Accordingly, it may be necessary in some circumstances to adjust the termination criteria (step 912, FIG. 9) and weights used to combine various factors into the performance criteria (step 1126, FIG. 11) to allow a limited number of false positive detections in each detection algorithm and/or reduce detection latencies, so that the combination will provide optimum results.

Alternatively, multiple detection algorithms can be optimized upon substantially simultaneously, with the aggregate collection of detection parameters from all of the applicable detection algorithms (including persistence and selective inversion for each algorithm) being used in the greedy line search algorithm described above. This would tend to prolong the automatic template development process (FIG. 9), as more parameters would need to be processed and the results would be less likely to converge as quickly.

In one embodiment of the invention, multiple detection channels can be used to detect a single event by identifying combinations of neurological conditions that occur in one or more locations of the patient's brain. For example, when one detection channel is used to detect a particular neurological event of interest, a second detection channel can be used to detect either a corroborative signal pattern or the absence of contradictory or confounding factors (such as noise). In this example, the second detection channel represents a "qualifying channel" with respect to the first detection channel. As described above, either stereotypical noise records or EEG records including noise can be annotated and used with the automatic template development process to enable the isolation and identification of the occurrence of noise; the same is true for other types of confounding factors (such as sleep spindles and other normal neurological signal patterns).

In general, a qualifying channel allows a detection to be made only when both channels are in concurrence with regard to detection of an event. For example, a qualifying channel can be used to indicate when a seizure has "generalized," i.e. spread through a significant portion of a patient's brain. To do this, a first input channel and a second input channel of the neurostimulator 110 (FIG. 1) are configured to receive EEG waveforms from separate amplifier channels coupled to electrodes in separate parts of the patient's brain (e.g., in opposite hemispheres).

Accordingly, then, a Boolean AND operation on the detection results of the channels will indicate a detection only when the first detection output and the second detection output both indicate the presence of an event. Alternatively, when Boolean logic inversion is present on the second detection channel, a detection is accomplished when the first detection output indicates the presence of a first event (e.g., the event sought to be detected) while the second detection output does not indicate a second event (e.g., noise). As described above, detection outputs can be provided with selectable persistence (i.e., the ability to remain triggered for some time after the event is detected), allowing the Boolean AND combination to be satisfied even when there is not precise temporal synchronization between detections on the two channels.

It should be appreciated that the concept of a "qualifying channel" allows the flexible configuration of a neurostimulator 110 according to the invention to achieve a number of advantageous results. In addition to the detection of generalization, as described above, a qualifying channel can be configured, for example, to detect noise so a detection output is valid only when noise is not present, to assist in device configuration in determining which of two sets of detection parameters is preferable (by setting up the different parameters in the first detection channel and the second detection channel, then replacing the Boolean AND combination with a Boolean OR combination), or to require a specific temporal sequence of detections (which would be achieved in software by the CPU 128 after a Boolean OR combination of detections). There are numerous other possibilities.

As with the combination of multiple detection algorithms, described above, it is presently considered preferable to perform template development on each detection channel as described above separately (or twice for each algorithm, to accommodate selective inversion), and then to combine the results via Boolean logic. Alternatively, multiple detection channels can be optimized upon substantially simultaneously, with the aggregate collection of detection parameters from all of the applicable detection channels (including persistence and selective inversion for each channel) being used in the greedy line search algorithm described above. This too would tend to prolong the automatic template development process (FIG. 9).

As described above, if the EEG records stored in the programmer 212 and used in the automatic template development process have not been pre-processed by the neurostimulator 110, it is possible to employ the automatic template development process to identify a suitable set of signal pre-processing parameters. Several approaches are possible, including optimizing on the signal pre-processing parameters substantially simultaneously with the detection parameters described above (as with optimization upon multiple detection algorithms, creating a relatively longer list of parameters to optimize upon), or alternatively first identifying a preferred set of detection parameters (with a default set of pre-processing parameters) and then identifying the preferred signal pre-processing parameters based on the desired detection parameters, or first identifying desirable signal pre-processing parameters and then the detection parameters.

In any of these cases, if pre-processing is performed in the analog domain in the neurostimulator 110, it may be necessary for the programmer 212 to simulate the results of such pre-processing digitally, and apply the simulated results to the EEG records being considered before detection is tested (as in FIG. 9). In one embodiment of the invention, signal pre-processing parameters are individually programmable for each EEG channel in the neurostimulator 110, or alternatively, a single set of signal preprocessing parameters may be programmed to have a global effect upon all channels.

The results obtained by the automatic template development process (FIG. 9) are ultimately presented and displayed to the clinician using the programmer 212 (step 520, FIG. 5). Various graphical aids may be used to assist the clinician in interpreting the results. For example, in addition to a basic numeric readout of the detection parameters making up the computed patient-specific template, it may be advantageous to provide a graphical display of the EEG records, illustrating where various correct and false detections occurred, and further illustrating where annotated events may have been missed. This may allow the clinician to revise the event annotations (as in FIG. 6) to more precisely specify the bounds of the events sought to be detected, to reclassify event types, or to otherwise change the inputs to the template development process of the invention, allowing it to be re-run for better results if necessary. Moreover, an excessively conservative detection scheme might not be preferred—it should be recognized that a relatively small number of false positive detections may be tolerable and in some circumstances desirable, as these false positives may actually represent latent seizure-like activity with only minor (if any) clinical manifestations.

Figure 12:
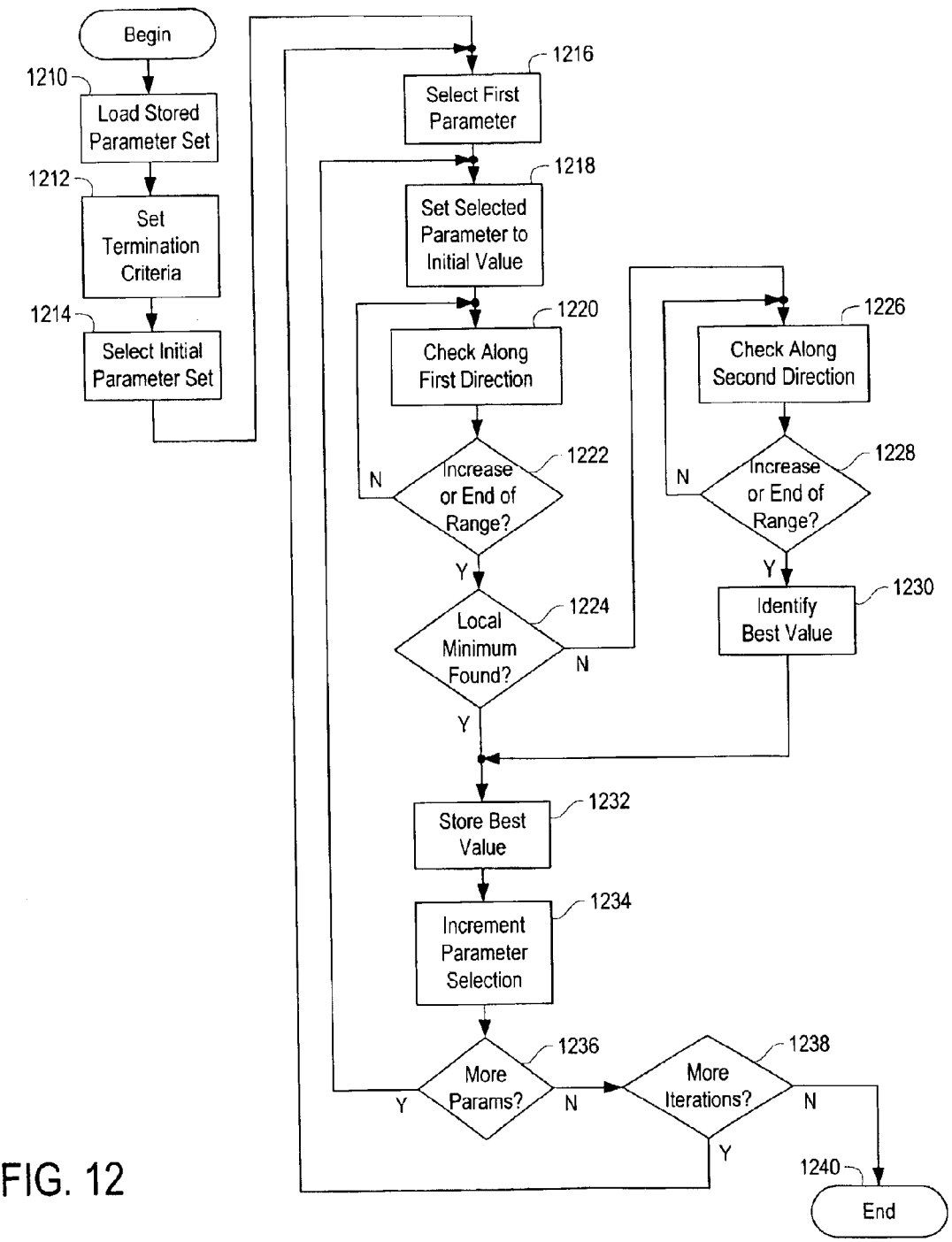
FIG. 12 is a flow chart illustrating the steps performed in a single local minimum variant of the Greedy Line Search of FIG. 9.

FIG. 12 sets forth a variation on the greedy line search method set forth in FIG. 9, in particular, one in which a single local minimum of the performance metric (FIG. 11) is sought, rather than a global minimum. It has been found that even in multiple dimensions, the performance metric tends to converge to a single minimum, and accordingly, the performance of the method set forth in this FIG. 12 (and in particular the running time) is greatly improved over the standard greedy line search.

The method begins by loading the stored parameter set (step 1210) with values that would not necessarily achieve successful detection results, typically a set of defaults having relatively low specificity. As above, criteria for determining whether a detection result is "successful," and specifically several components that are combined into a performance metric, are described in connection with FIGS. 10–11. The stored parameter set generally takes the form of a data structure that ultimately can be downloaded to and used by the implantable neurostimulator 110, though it should be noted that a translation step can alternatively be performed later to convert the stored parameter set into data recognizable by the neurostimulator 110. As with the method of FIG. 9, the user, typically a clinician, then has an opportunity to set termination criteria (step 1212), to specify how certain a parameter set must be before the method of FIG. 12 may terminate (e.g., one or more convergence bounds or a limit on permitted iterations). The user may also select various weights for the various components of the performance metric at this stage.

An initial parameter set is then selected (step 1214). Initial values for each parameter may be taken from the loaded parameter set (step 1210) or heuristically calculated or preprogrammed default parameters expected to produce advantageous results. For example, where no loaded parameter set is available, for some parameters, such as minimum peak-to-peak voltage, minimum wave duration, and others, initial parameters may be derived by heuristic analysis of annotated event records—e.g., slightly more than the average wave characteristics during annotated seizures. For other parameters, such as half wave analysis window size, line length window size, and others, initial parameters may be derived from pre-programmed values as above—e.g., a line length window size of thirty-two processing windows may be a useful starting point. Alternatively, all parameters may be initially selected from pre-programmed defaults.

In the disclosed embodiment of the invention, preprogrammed default parameters are as follows (all assuming a 4 millisecond sampling interval): minimum half wave amplitude is 40 10-bit amplitude units (searched over a range of 0 to 1016 in steps of 8); minimum half wave duration is 13 samples (searched over a range of 0 to 250 samples in steps of 1); half wave analysis window size is 500 milliseconds (searched over a range of 40 to 3,000 milliseconds samples in steps of 10); the qualified half wave count threshold is 4 (searched over a range of 2 to 33 in steps of 1); detection analysis window size is 8 processing windows (searched over a range of 1 to 16 processing windows in steps of 1); and the qualified analysis window count threshold is 3 qualified processing windows (searched over, a range of 1 to 16 in steps of 1).

The first parameter in the parameter set (in the disclosed embodiment, minimum amplitude) is then selected (step 1216); this parameter will be varied in subsequent steps to determine its best value. The selected parameter is set to an initial value (step 1218), which in an embodiment of the invention is the value the parameter currently holds (e.g., either from the initial parameter set of step 1214 or from previous iterations of the method). The value of the parameter is then advanced in a first direction (e.g. incremented) while observing the performance metric (step 1220). This is continued as long as the performance metric continues to exhibit enhanced performance (a substantially constant or decreasing value of the metric)—that is, until the performance metric shows an increase or an incomputable value, or the end of the parameter's range is reached (step 1222). If the initial parameter value yields an incomputable performance metric value (for example, when a constraint in the calculation of the performance metric is violated), then succeeding values continue to be checked until the value is incomputable or an end-of-range is reached. If no local minimum has been found (i.e., there has been no decrease in the value of the metric followed by an increase (step 1224), then the values of the parameter are checked in the other direction. Otherwise, the process continues with step 1232 as described below.

Accordingly then, beginning again with the initial value, the value of the parameter is advanced in a second direction (e.g. decremented) while observing the performance metric (step 1226). This is continued as long as the performance metric continues to exhibit enhanced performance (a substantially constant or decreasing value)—that is, until the performance metric shows an increase or an incomputable value, or the end of the parameter's range is reached (step 1228). Again, if the initial parameter value yields an incomputable performance metric value, then succeeding values continue to be checked until the value is computable or an end-of-range is reached.

The best-performing value of the parameter along the second direction is then identified (step 1230). Generally, if a local minimum is found along the second direction, this value is selected. In some cases, even after checking both directions, no single local minimum in the performance metric is found. For example, in some circumstances, the performance metric might be incomputable or substantially constant over the entire range of a parameter's values (given a certain combination of other parameters). In this case, the initial parameter value is retained. Under certain other circumstances, the performance metric might be incomputable over a portion of a range; in this case, incomputable values are treated as the end of the parameter's range. If the performance metric is substantially constant over a range that would otherwise be a local minimum, the parameter value closest to the starting point is selected as the local minimum for purposes of the present method.

The best value from either direction, the first direction or the second direction, is then stored in the parameter set (step 1232). The parameter selection is then incremented (step 1234), thereby choosing the next parameter in the parameter set, and as long as there are more parameters to modify (step 1236), the newly selected parameter is set to its initial value (step 1218), and that parameter is tested as described above over a range of values in both directions (if necessary) from its initial value, along with the other parameters in the stored parameter set.

If there are no more parameters to consider (step 1236), the stored parameter set is compared to the parameter set stored after the prior iteration (or at the outset, step 1210, if only one pass through the method has been completed). If the stored parameter set has converged sufficiently (step 1238) according to the termination criteria set by the user in step 1212, or if it appears that it will not converge or is oscillating among multiple solutions, then the process ends (step 1240), and the most recent stored parameter set is used in the patient-specific detection template. Otherwise, if the process is not able to end, the first parameter is again selected (step 1216), and the iterative process repeats until convergence (relative to the prior iteration) is achieved or until a pre-defined or programmed number of iterations have been performed (which may indicate that no solution is possible given the specified initial parameter set and termination criteria). It has been found that convergence is usually obtained after four or fewer iterations; accordingly, causing the procedure to terminate after five or six iterations should provide satisfactory results. It should also be noted that testing for convergence (step 1238) can be performed at other times during the process illustrated in FIG. 9, for example after each "line" in the greedy line search is completed and all values for a parameter have been tested (between steps 1232 and 1234).

It should be noted that the single-local-minimum method illustrated in FIG. 12 is relatively "myopic" in comparison to the greedy line search of FIG. 9, in that the method of FIG. 12 searches only for a local minimum in the function defined by the performance metric—it stops searching each variable once it has found a trough. This will generally result in a more efficient search of parameter space, but it will not necessarily converge to the same solution as the greedy line search of FIG. 9. The single-local-minimum method of FIG. 12 may converge to a solution that is either better or worse than a solution found by the greedy line search method of FIG. 9, depending on the circumstances; no universal relationship between the two is known.

For the line length and area measurement tools described above, an alternative to the greedy line search of FIG. 9 (and its single-local-minimum relative of FIG. 12) exists that provides greatly enhanced optimization performance and good results. This method, deemed a "feature overlay" method, is graphically illustrated in FIG. 13.

An "overlay feature" is selected from existing feature (e.g., line length or area) or calculated, for example by evaluating a function representative of the difference (or ratio) between a feature being measured (in the disclosed embodiment, line length or area) and that feature's long-term trend. The calculated overlay features from a set (preferably all available) EEG records are superimposed to produce a feature overlay. In a system according to the invention this feature overlay is used to differentiate between event-containing records and baseline records.

Figure 13:
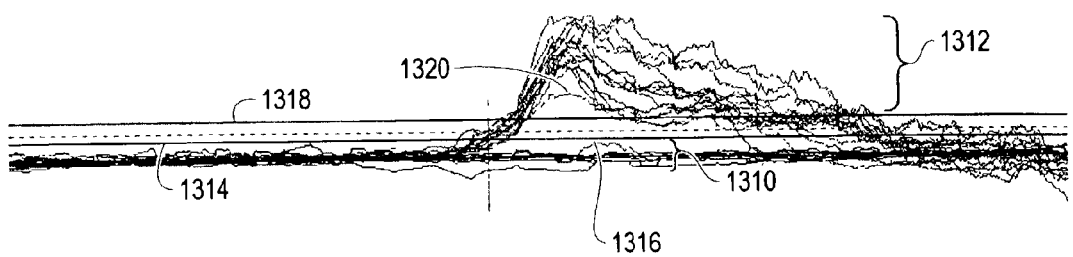
FIG. 13 is a graph illustrating an exemplary line length feature overlay calculation on baseline and seizure-containing EEG records.

FIG. 13 presents a graph of a line length overlay feature calculated on a plurality of baseline records 1310. These traces are calculated by subtracting the calculated line length value from the then-current normalized line length trend (calculated as generally described above and as specifically set forth below); the horizontal axis is time. A graph of line length overlay feature is also calculated on a plurality of seizure-containing records 1312. In both cases, values for the line length trend window size, trend inter-sample interval, and number of trend windows are fixed at values found to be advantageous for the widest variety of patients, although it is possible for a clinician or other system user to alter those values and re-run the feature overlay process according to the invention.

Accordingly, if only baseline records are available to a system according to the invention, a first threshold level 1314 can be set to be slightly higher than a maximum 1316 line length value selected from all of the baseline traces 1310. Similarly, once one or more event-containing records 1312 becomes available, a second threshold 1318 can be set to be between the maximum baseline line length value 1316 and a minimum peak event-containing line length value 1320 (that is to say, the lowest of the maxima selected from each event-containing trace). These calculations will be described in further detail below, in connection with FIGS. 17–18. If the minimum peak event-containing line length value 1320 is lower than the maximum baseline line length value 1316, then the threshold may be set equal to or higher than the maximum baseline 1316 (in which case false negatives might result) or equal to or lower than the minimum peak event-containing line length 1320 (in which case false positives might result).

It should be recognized that this feature overlay might not work in all cases; other parameters (in addition to the threshold level described above, such as trend calculation parameters) may need to be varied, or there might not be an observable difference between baseline and event-containing records. In this case, false positive or false negatives might be relatively prevalent, suggesting that another detection approach (e.g., using a different detection channel, combination of detection tools, or varying other detection parameters) should be used instead.

It should be noted that the specific amplitudes, thresholds, and intervals depicted in FIG. 13 are for purposes of illustration only and are not intended to be to scale.

Figure 14:
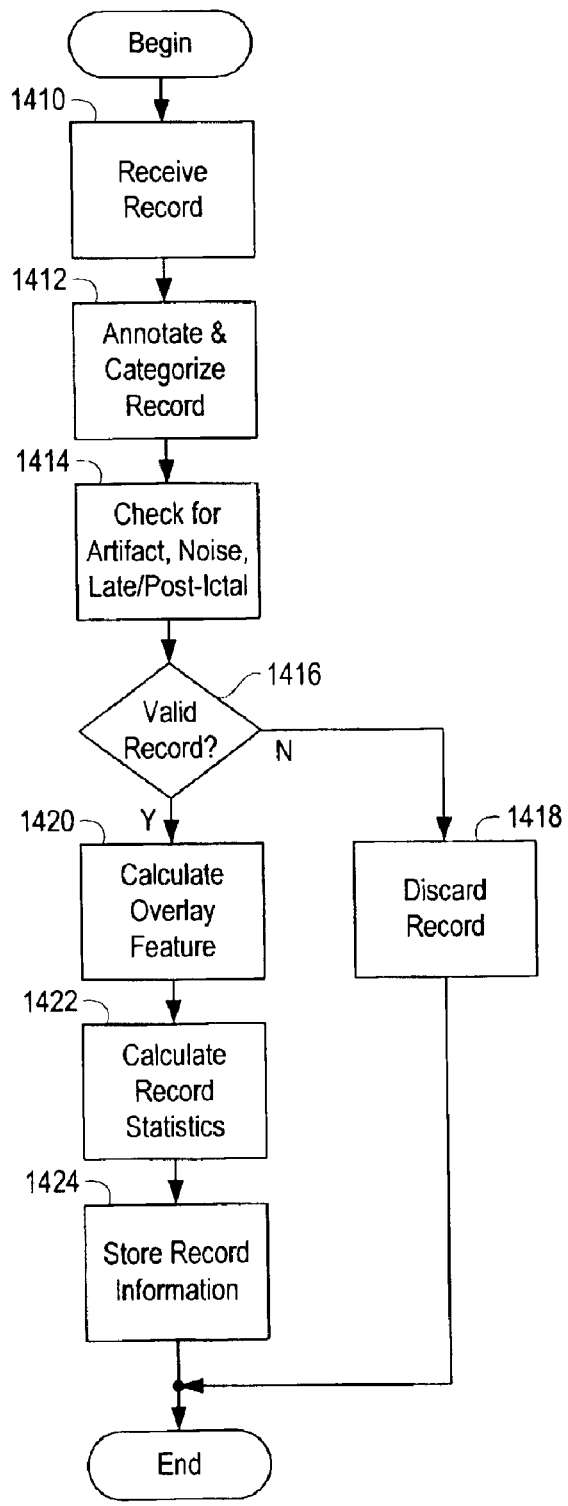
FIG. 14 is a flow chart illustrating the steps performed in processing EEG records for feature overlay calculation according to an embodiment of the invention.

FIG. 14 illustrates a method by which records containing electrographic information are received and processed for feature overlay (and other parameter development techniques) by a system according to the invention. Initially, an EEG record is received (step 1410) by the programmer 212 (FIG. 2); it can be uploaded from the implantable neurostimulator 110 (FIG. 1) or obtained elsewhere, and it is pre-processed as desired. The record is then annotated (if it has not been already) and categorized (step 1412) into one of several possible categories, such as baseline (i.e., the record does not contain any seizure or other event-related data of interest), event-containing (there is a seizure or other event represented within the data), or in an embodiment of the invention, other (which should not be used for training a system according to the invention). Categorization can be performed via manual annotation (as in FIG. 5, step 512) or via an automatic algorithm, such as a clustering algorithm.

The newly obtained record is then checked (step 1414) for the presence of an artifact (such as from delivery of a stimulation signal by either the implantable neurostimulator 110 or other equipment), noise, or late/post-ictal content (which preferably is not used in training in order to avoid late detections), and insufficient record length. This check may result in the invalidation or recategorization (e.g., from event-containing to baseline) of the record, and will be described in further detail below in connection with FIG. 16.

If the record is not valid (step 1416) for any of the reasons set forth above or any applicable other reason, the record is discarded (step 1418) and is not used for any further parameter set training or template development according to the invention. For example, a record will also be discarded if it is too short for a feature to be calculated, or if an annotation is positioned too near to the beginning or the end of the record to allow the methods set forth below to succeed.

If, on the other hand, the record is valid (step 1416), the overlay feature function is calculated for the record (step 1420); this operation will be described in detail below with reference to FIG. 17. The statistical characteristics of the record are measured and calculated (step 1422) for future calculations, and to ultimately determine whether the record is a statistical outlier that should be ignored (see FIG. 15, below). In particular, in the disclosed embodiment of the invention, each record's single-record overall maximum overlay feature value (or, for event-containing records, the maximum overlay feature value within a definable time band around the annotation of onset) is calculated. Outlier identification (including the statistics involved) will be treated in detail below with reference to FIG. 20.

Any desired information relating to the valid record is then stored (step 1424) for future use, including its statistics, raw or processed electrographic data, overlay feature data, and possibly additional information as desired.

Figure 15:
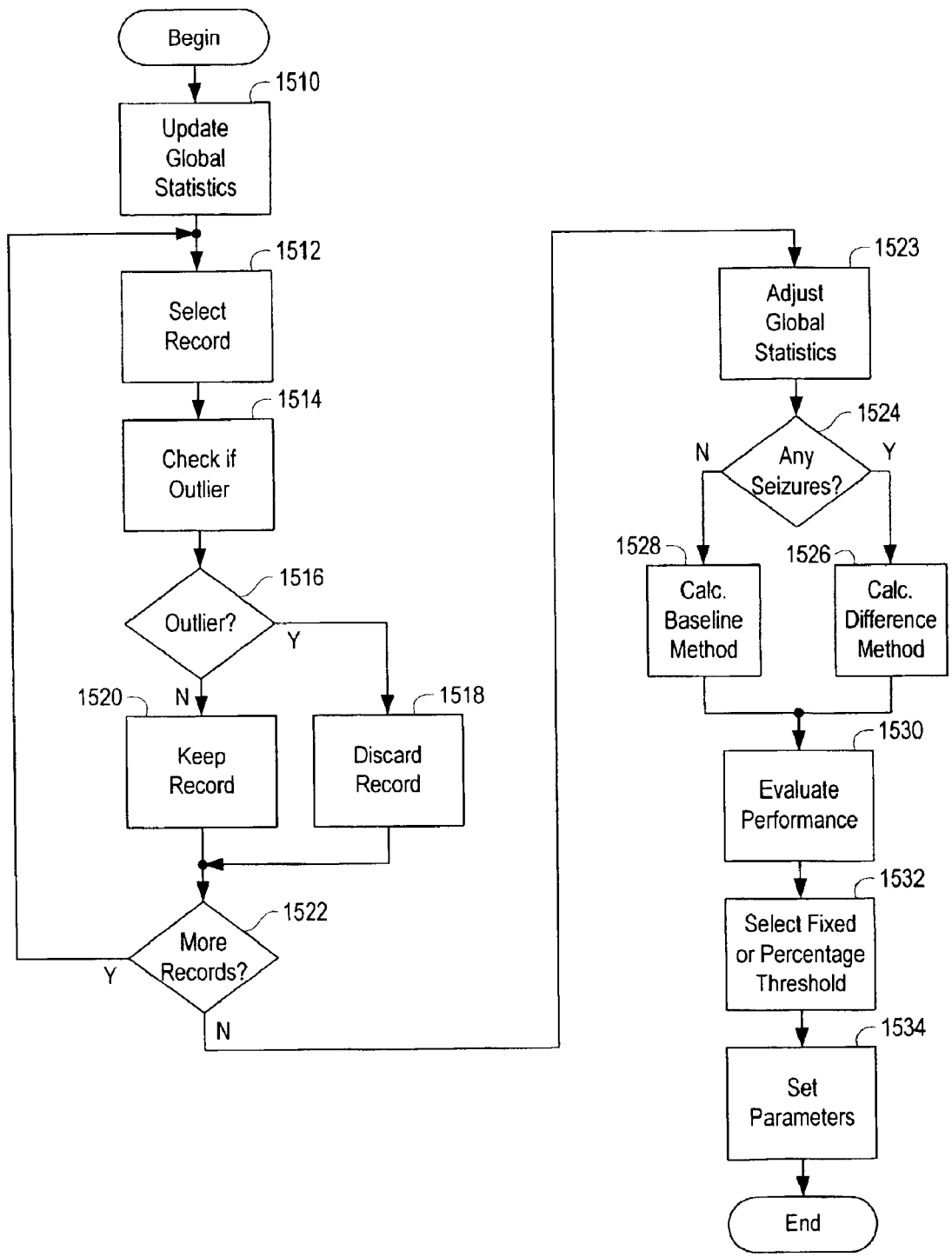
FIG. 15 is a flow chart illustrating the steps performed in performing a feature overlay optimization of detection tool parameters according to an embodiment of the invention.

In an embodiment of the invention, the process by which feature overlay is calculated on a group of pre-processed and pre-categorized records is illustrated in FIG. 15.

Global statistics pertaining to the categorized records are initially updated (step 1510). In particular, and for purposes of outlier identification, certain statistics are maintained for each category of record (in the disclosed embodiment, baseline or event-containing) and for each threshold type (in the disclosed embodiment, fixed offset or percentage offset). Both overall mean and overall standard deviation values are calculated over all records' individual single-record maxima, resulting in an overall mean-of-maxima and standard-deviation-of-maxima for each category of record. These statistical values are updated for each new record processed, regardless of whether the new record is an outlier, and are categorized by detection tool type and threshold type. Accordingly, in the disclosed embodiment, there are four categories of statistics: fixed-offset baseline records, fixed-offset event-containing records, percentage-offset baseline records, and percentage-offset event-containing records. Additional statistics are also measured for later threshold calculation (steps 1526–1528, below), including the overall maximum, and overall minimum of each record's single-record maximum overlay feature values.

Each record is then considered separately to identify outliers. A record is selected (step 1512) and analyzed to determine whether it is an outlier (step 1514); this is illustrated in detail below with reference to FIG. 20. If the record is an outlier (step 1516), it is discarded (step 1518) and not used for training; in the disclosed embodiment of the invention. If the record is not an outlier (step 1516), the record is kept in the appropriate category (step 1520), typically baseline or event-containing (e.g. seizure).

If there are more records to process (step 1522), another record is selected (step 1512) and the outlier rejection process continues. Otherwise, the global statistics are adjusted to account for any discarded outliers (step 1523). For example, if the overall maximum and overall minimum had come from outlying records (which is likely), those values will be recalculated in the absence of the outliers.

The following steps are all performed on the aggregate collection of records, updating feature-overlay-based parameter values according to any new records processed and categorized in the foregoing steps.

If there are any seizures (step 1524) or other events of interest to be trained in the collection of EEG records obtained (including any newly obtained records), then detection thresholds are calculated based on the overlay feature maxima (step 1526). This process is documented in FIG. 18 and will be described in further detail below. If there are no event-containing records (step 1524), detection thresholds are calculated based only on baseline records (step 1528). This procedure is illustrated in FIG. 19 and will be described in additional detail below. In either case, both a fixed offset threshold and a percentage offset threshold are calculated.

After the two possible threshold values have been calculated by a system according to the invention, the thresholds are evaluated (step 1530) via a performance metric (such as the performance metric described above, with reference to FIG. 11, or any other applicable performance metric). The threshold, fixed or percentage, that provides the best performance is then selected (step 1532), and the corresponding parameters are stored and set (step 1534) for later use, review, or download to the implantable neurostimulator 110.

Figure 16:
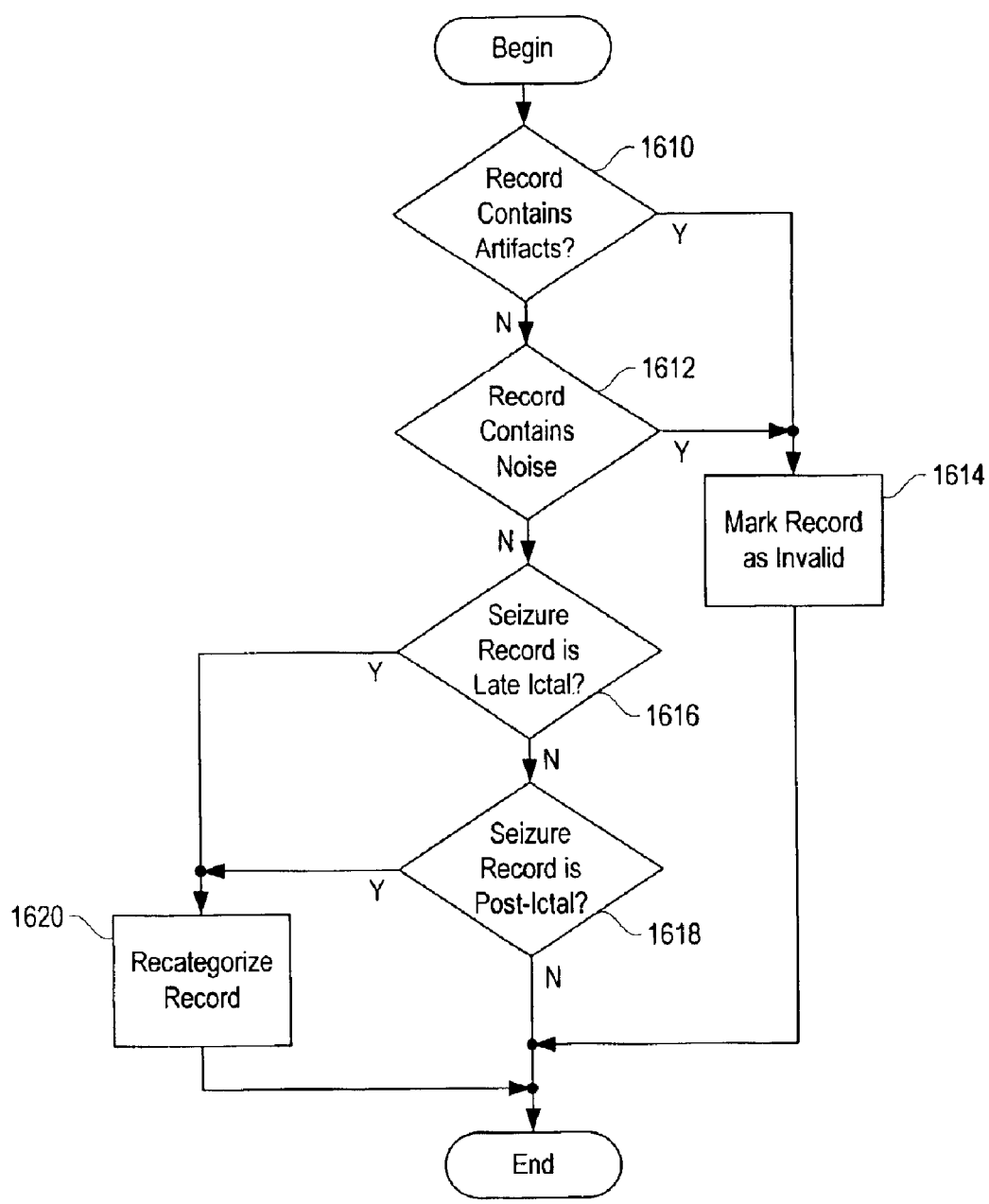
FIG. 16 is a flow chart illustrating the steps performed in determining whether an EEG record is valid and properly classified in an embodiment of the invention.

A method according to the invention for identifying artifacts, noise, and late/post-ictal activity (FIG. 14, step 1414) is illustrated in FIG. 16. Initially, a newly received record is checked for artifacts (step 1610) and noise (step 1612). If the record contains a substantial level of artifacts (such as amplifier blanking effects, invalid data from mode switching, etc.) or noise (such as RF interference or other undesired extrinsic influences), the record is marked as invalid (step 1614) and is not used to train a system according to the invention.

A valid event-containing (seizure) record is then checked to determine whether it represents late ictal activity (step 1616). Late ictal activity is ictal activity that occurs a significant amount of time, for example one or more minutes, after an annotated seizure onset. Preferably, this electrographic data is not used to train an onset detector, as it may result in a loss of specificity with regard to onset patterns. Similarly, an event-containing record is checked to determine whether it contains post-ictal activity (step 1618), namely post-seizure electrographic activity that may have some epileptiform features. Preferably, post-ictal activity should also be ignored to maintain specificity. In an embodiment of the invention, event-containing records containing late ictal activity or post-ictal activity are recategorized as baseline records (step 1620); alternatively, they may be marked as invalid and not used to train an event detector according to the invention.

Figure 17:
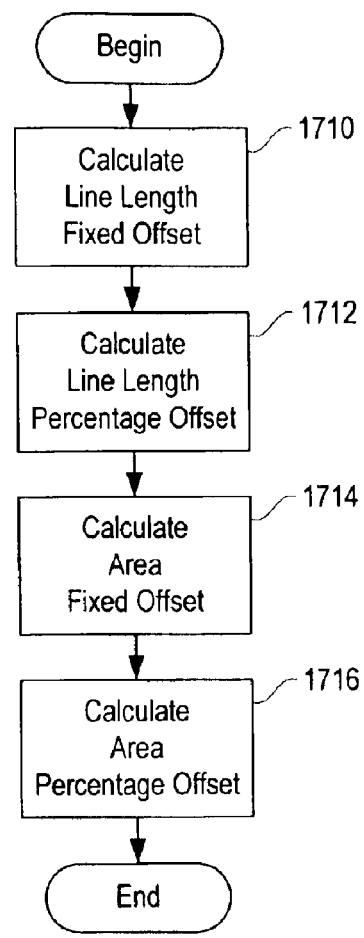
FIG. 17 is a flow chart illustrating the sequence of steps performed in calculating overlay feature function values according to an embodiment of the invention.

A method for calculating an overlay feature (FIG. 14, step 1420) is illustrated in detail in FIG. 17. In the disclosed embodiment of the invention, the feature overlay optimization technique is used to tune two detection tools, a line length-based detection tool and an area-based detection tool, both of which are described in additional detail above. And as observed above, the feature overlay method is used to obtain a threshold to which the difference or ratio of short-term observations and long-term trends are compared.

The method begins by generating an overlay feature for the line length fixed offset threshold (step 1710). For each processing time window in a newly obtained record, a normalized long-term line length trend is subtracted from a short-term line length value. In the disclosed embodiment of the invention, the short-term line length value is calculated over a length of 128 to 4096 milliseconds in power-of-two steps (corresponding to 1 to 32 processing time windows). The default is the maximum of 32 processing time windows; this has been found to provide good results across a wide patient population. Similarly, the long-term line length trend is calculated over a multiple (2 to 256 in power-of-two steps) of periods of 128 to 4096 milliseconds in power-of-two steps, each period separated by approximately 4 to 600 seconds (4 to 60 seconds in approximately four second intervals, and 90 to 600 seconds in approximately 30 second intervals—these time periods are all multiples of a single 128 ms window). In the disclosed embodiment, the long-term line length trend includes sixteen periods, each 4096 milliseconds (32 windows) in length with their starting times separated by 4096 milliseconds. Because the periods are 4096 milliseconds in length and also 4096 milliseconds apart, in this example, they are consecutive.

The value of the difference between the short-term line length observation and the long-term trend is the overlay feature value for the line length fixed offset threshold. Similarly, an overlay feature for the line length percentage offset threshold is then calculated (step 1712) as the short-term line length value divided by the normalized long-term line length trend, then subtracting one and multiplying by 100 to scale into percentage-change units. For the latter calculation, the default parameter values are the same as for the fixed offset threshold calculation.

Essentially the same calculations are carried out for the area-based detection tool. First, an overlay feature for the area fixed offset threshold (step 1714) is calculated. For each processing time window in a newly obtained record, a normalized long-term area trend is subtracted from a short-term area value. In the disclosed embodiment of the invention, the short-term area value is calculated over a length of 128 to 4096 milliseconds in power-of-two steps (corresponding to 1 to 32 processing time windows). The default is the maximum of 32 processing time windows; this has been found to provide good results across a wide patient population. Similarly, the long-term area trend is calculated over a multiple (2 to 256 in power-of-two steps) of periods of 128 to 4096 milliseconds in power-of-two steps, each period separated by approximately 4 to 600 seconds (4 to 60 seconds in approximately four second intervals, and 90 to 600 seconds in approximately 30 second intervals—these time periods are all multiples of a single 128 ms window). In the disclosed embodiment, the long-term area trend includes sixteen periods, each 4096 milliseconds (32 windows) in length and separated by 4096 milliseconds.

The value of the difference between the short-term area observation and the long-term trend is the overlay feature value for the area fixed offset threshold. Similarly, an area percentage offset threshold is then calculated (step 1716) as the short-term area value divided by the normalized long-term area trend, then subtracting one and multiplying by 100 to scale into percentage-change units. For the latter calculation, the default parameter values are the same as for the fixed offset threshold calculation.

It is important to observe that the EEG records upon which the foregoing trends and observations are calculated need to be sufficiently long for trends to develop before any event occurs. That is, the pre-trigger recording time for the implantable neurostimulator 110 needs to be long enough that the event occurs partway through the record, with enough electrographic data prior to the event to allow trends to settle down.

Figure 18:
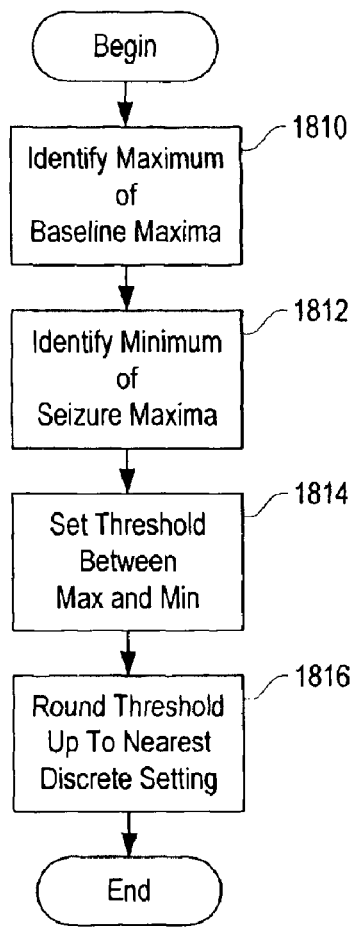
FIG. 18 is a flow chart illustrating the sequence of steps performed in calculating feature overlay fixed offset and percentage offset thresholds with baseline and seizure data according to an embodiment of the invention.
Figure 19:
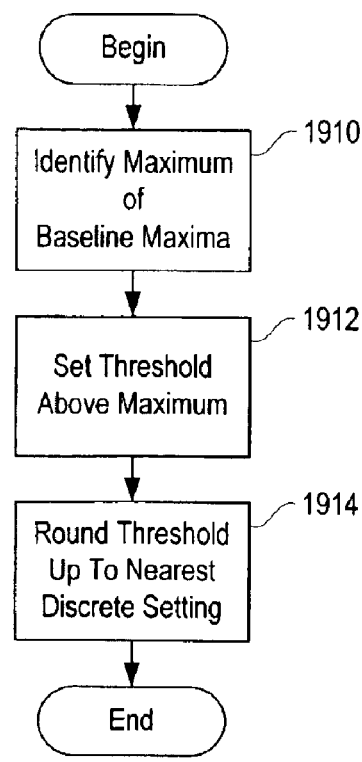
FIG. 19 is a flow chart illustrating the sequence of steps performed in calculating feature overlay fixed offset and percentage offset thresholds with only baseline data according to an embodiment of the invention.

The difference method of selecting threshold parameter values according to the invention (FIG. 15, step 1526) is illustrated in detail in FIG. 18. This method operates by analyzing the previously-calculated statistics (FIG. 14, step 1422, and FIG. 15, step 1510) of a set of EEG records that includes both baseline and event-containing records. Initially, an overall maximum overlay feature value, selected from the set of all single-record overlay feature maxima taken from baseline records, is identified (step 1810), i.e., the maximum of the set of maxima. For event-containing records, a region (in the disclosed embodiment, ±12.8 seconds) is defined around the annotated seizure onset within the record. Within this region, the overlay feature's single-record maximum is determined. From the set of these single-record maxima, the overall minimum overlay feature value of all single-record feature maxima taken from event-containing records, is then also identified (step 1812), i.e., the minimum of the set of maxima. As noted, both of these values have previously been calculated (FIG. 15, step 1510).

The threshold parameter value is then set an interval between the previously-calculated maximum feature value and minimum feature value (step 1814). In one embodiment of the invention, the interval is halfway between the minimum and the maximum. In other embodiments, the interval may be 5% between the minimum and the maximum, or 10%; other values are, of course, possible. The interval may be predetermined or selected by a user of a system according to the invention. The specific interval used represents a tradeoff in detection performance between false positives and detection latency (delay); a smaller interval will generally yield more false positives with less delay, while a larger interval will generally yield fewer false positives but with more delay.

Thresholds are rounded up to the closest available programmable value (step 1816) for the implantable neurostimulator 110, which as disclosed for a fixed offset threshold includes the range of −1600 units to 1600 in steps of eight units, and for a percentage offset value includes the range of −87.5% to 500% in steps of 12.5%.

In an embodiment of the invention, the sequence of steps set forth in FIG. 18 is performed at least twice: once for the fixed offset threshold (using statistics obtained from the fixed offset version of the overlay feature calculations, via steps 1710 and 1714 of FIG. 17), and once for the percentage offset threshold (using statistics obtained from the percentage offset version of the overlay feature calculations, via steps 1712 and 1716 of FIG. 17). If both line length and area detection tools are used, the steps of FIG. 18 may be performed four times: once for each of four possible combinations of tool and threshold type.

The baseline method of setting thresholds according to the invention (FIG. 15, step 1528) is illustrated in detail in FIG. 19. This method operates by analyzing the previously calculated statistics (FIG. 14, step 1422, and FIG. 15, step 1510) obtained from the set of EEG records that includes only baseline records (for example, if no seizure or other event has yet been recorded by the implantable neurostimulator 110). Initially, the maximum value of all maxima of baseline records is identified (step 1910). As noted, this value has previously been calculated (FIG. 15, step 1510).

The threshold is then set five percent (5%) above the previously-calculated maximum value (step 1912). Thresholds are rounded up to the closest available programmable value (step 1914) for the implantable neurostimulator 110, which as disclosed for a fixed offset threshold includes the range of −1600 units to 1600 in steps of eight units, and for a percentage offset value includes the range of −87.5% to 500% in steps of 12.5%.

In an embodiment of the invention, the sequence of steps set forth in FIG. 19 is performed at least twice: once for the fixed offset threshold (using statistics obtained from the fixed offset version of the overlay feature calculations, via steps 1710 and 1714 of FIG. 17), and once for the percentage offset threshold (using statistics obtained from the percentage offset version of the overlay feature calculations, steps 1712 and 1716 of FIG. 17). If both line length and area detection tools are used, the steps of FIG. 19 may be performed four times: once for each of four possible combinations of tool and threshold type.

Figure 20:
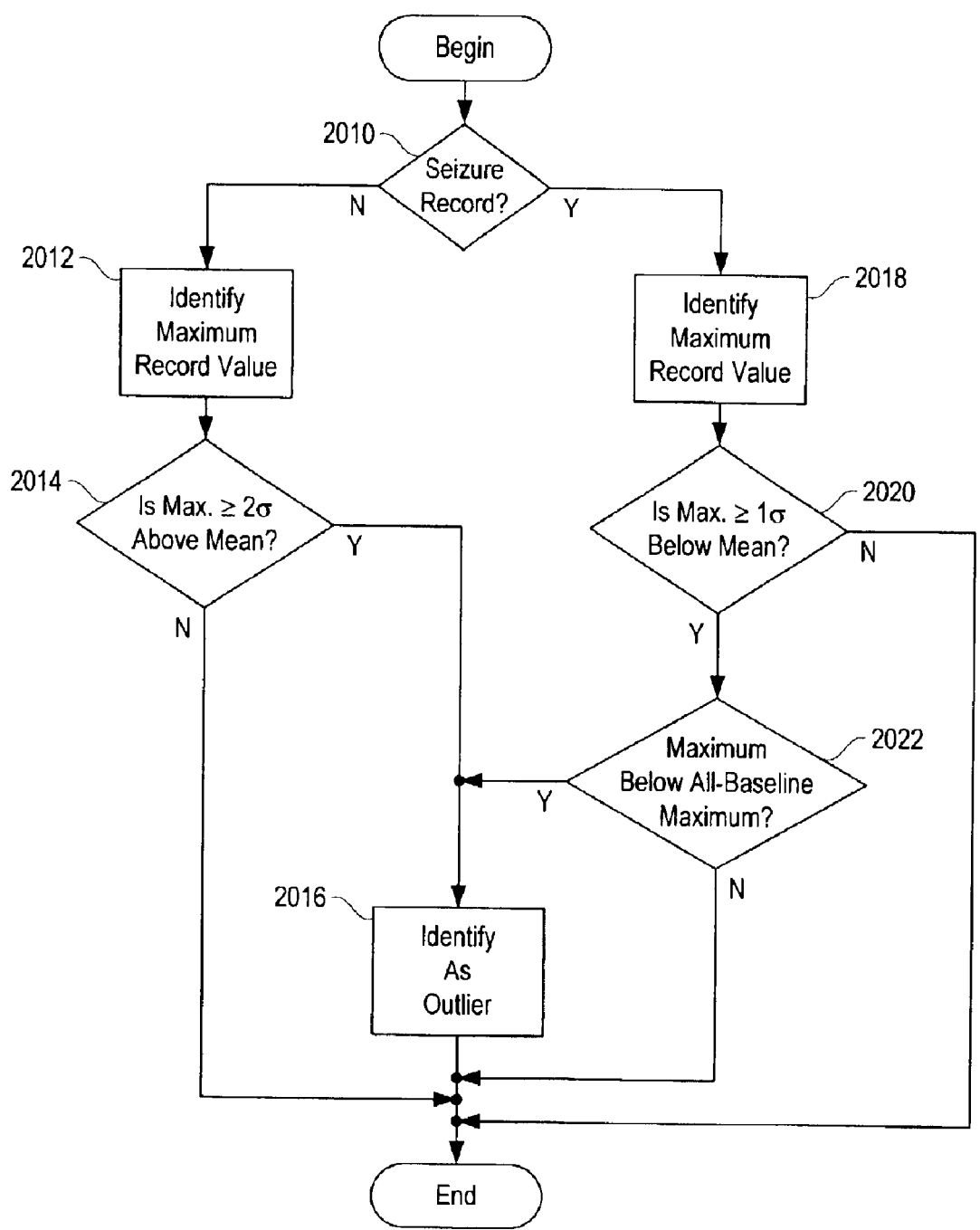
FIG. 20 is a flow chart illustrating steps performed in identifying outlying EEG records according to an embodiment of the invention.

Turning now to FIG. 20, a method for identifying outlying baseline and event-containing (e.g. seizure) records (FIG. 15, step 1514) is illustrated in detail. Baseline and seizure records are treated differently (step 2010). For a baseline record, the maximum value of the overlay feature function (see, e.g., FIG. 13) is identified (step 2012). If the maximum value for a record is greater than or equal to two standard deviations ($2\sigma$) above the mean of other like records' maxima (step 2014), then the new record is identified as an outlier (step 2016). Similarly, for a seizure record, the maximum value of the overlay feature function (FIG. 13) is identified (step 2018). If the maximum value for the record is greater than or equal to one standard deviation (1σ) below the mean of other like records' maxima (step 2020), and in an embodiment of the invention if the maximum value for the record is below the maximum of the other like records' maxima (step 2022), then the new record is identified as an outlier (step 2016).

If the latter criteria is met (the maximum value is below the maximum of other records' maxima), may be advantageous in an embodiment of the invention to measure the prevalence of false positives (or the performance metric in general) both with and without the questionable EEG record. If better performance is achieved by keeping the record, it should not be marked as an outlier.

As with other methods described herein, the steps of FIG. 20 may be performed up to four times: once for each possible combination of detection tool (two are disclosed) and threshold type (two are disclosed).

It should be noted that outliers are used to update statistics used in accordance with the of the invention, but are not used for threshold development.

Figure 21:
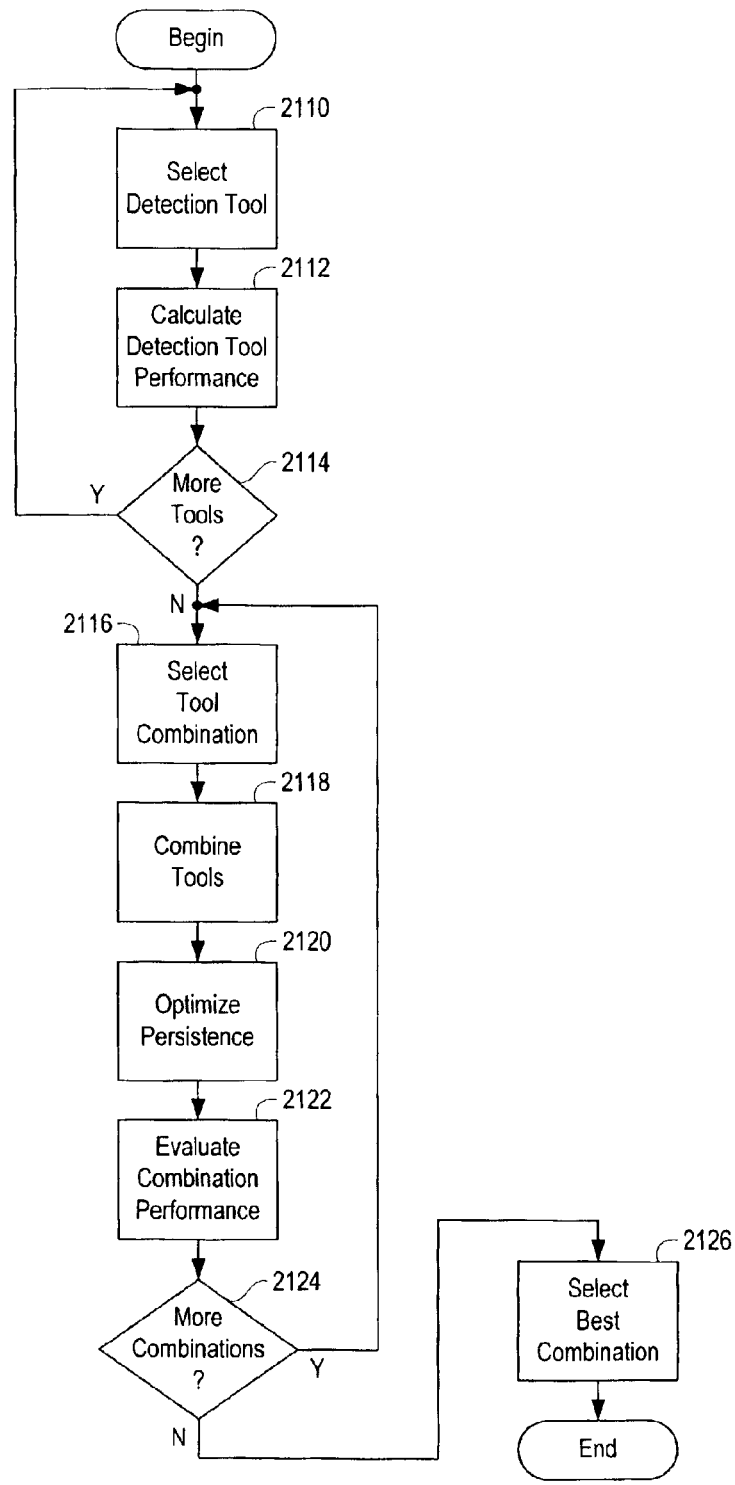
FIG. 21 is a flow chart illustrating how detection tools are advantageously combined to provide optimized performance according to an embodiment of the invention.

FIG. 21 is a flow chart illustrating in detail a method by which different detection tools according to the invention can be combined to identify the best possible combination of tools and persistence. In the context of this description, the terms "optimize" and "optimization" are intended to refer to achieving a desirable and advantageous balance between detection performance (with regard to a defined performance metric, such as the one described above with reference to FIG. 11) and realistic processing time with limited manual intervention, and not necessarily the best possible overall performance. Accordingly, long exhaustive searches of parameter space and other inefficient approaches generally are not deemed to provide optimization as the term is used herein.

It will be recognized that in the disclosed embodiment of the invention, three different detection tools can be used alone or in combination: a half wave based detection tool, a line length based detection tool, and an area based detection tool.

One of the possible detection tools is initially chosen (step 2110). The performance of the chosen tool is then calculated (step 2112) as described above. Specifically, and preferably, the half wave tool (if selected) is optimized by the single local minimum greedy line search described above (FIG. 12), while the line length and area tools are optimized via the feature overlay process described above (FIG. 15). The process of choosing a tool and calculating its performance is repeated (step 2114) for each possible tool in a combination, in the disclosed embodiment three times. It should be noted that it is generally advantageous to optimize the performance of each tool ahead of time (and in advance of the remaining steps of the procedure illustrated in FIG. 21) so the calculations do not need to be repeated for each iteration through the subsequent combination of detection tools of FIG. 21. Accordingly, if detection tool performance has already been calculated (for example, as described in connection with FIG. 15), there is no need to recalculate the performance (provided no new EEG records have been received). This kind of algorithm optimization is a routine design consideration and will be known to an individual of ordinary skill in the art of designing systems akin to the one described herein.

After all of the detection tools have been optimized individually (steps 2110–2114), one of the possible tool combinations is selected (step 2116). In the disclosed embodiment, there are seven possible combinations: each tool taken separately (three possibilities), two-tool combinations (three possibilities), and all three together. In a preferred embodiment of the invention, a clinician or other operator of a system according to the invention would be provided with an opportunity to "de-select" either individual tools or specific combinations of tools; those tools or combinations would then be removed from consideration by the method of FIG. 21.

The selected tool combination (from step 2116) is then integrated into one detection output (step 2118) by performing a Boolean operation on the individual tool detections, as described above. Persistence for each tool is then optimized (step 2120) through a search of potential persistence values applied to each detection tool in the combination (preferably performed via a form of the greedy line search described above in connection with FIGS. 9 and 12 or another optimized search strategy, but given the limited parameter space, an exhaustive search is also possible). As the detection tool performance is already calculated (step 2112 or earlier), this is accomplished simply by applying persistence to "stretch" each individual detection. For this operation, the performance metric combines block false positives, block false negatives, and delay.

The delay contribution to the performance metric comes from the time difference between the unequivocal electrographic onset (UEO) of a seizure or other event, as annotated, and the detection made by a system according to the invention. This delay value may be either positive (detection after the UEO) or negative (detection before the UEO); this value is constrained to within a defined or programmable time band around the UEO (values outside of the band are mapped to the extremes). Relatively small values of negative delay actually are preferred as they tend to be predictive of the annotated onset. In the disclosed embodiment of the invention, the delay contribution to the performance metric is weighted relatively lightly, so that the number of false positives and the number of false negatives are the primary factors.

In an alternative embodiment of the invention, delay is transformed into a normalized (−1 . . . 1) representation of the position within the time band. Accordingly, for purposes of the invention, detections within a selectable first time band before the UEO are normalized between −1 (earliest detection within the band) and 0 (detection at the UEO), and detections within a selectable second time band after the UEO are normalized between 0 (detection at the UEO) and 1 (latest detection within the band). The two selectable time bands need not be symmetric. This normalized delay factor is then weighted as desired (and as described above) and combined with the other contributions to form a scalar performance measure.

The selected tool combination is then evaluated (step 2122) by calculating its performance (via the block and delay performance metric set forth above) and storing that performance value for comparison to other tool combinations. It should be noted that preferably, the same combination of EEG records is analyzed for each tool combination, thereby allowing the most direct comparisons to be made. In some cases, this may require some records to be discarded as invalid (FIG. 14, step 1418) even though the only active detection tool or tools in a combination would be able to use them—this would be necessary when another detection tool in another combination would reject the records.

If there are more tool combinations to check (step 2124), the process is repeated by selecting another tool combination (step 2116) and proceeding.

Once all tool combinations have been checked, the best combination is selected (step 2126) by ranking the tool combinations by performance, outputting the various performance metric contributions (false positives, false negatives, and delay in an embodiment of the invention), and allowing the user to select the desired combination. Selection of the best combination can also be done alternatively (and automatically) by simply identifying the tool combination that yielded the best performance metric value. The selected tool combination (and all of the parameters for the individual tools, persistence, etc.) are then made available for download to the implantable neurostimulator 110. While the search methodology set forth above is presently preferred and effective, it should be recognized that in certain circumstances it may be advantageous to combine detection tools in such a way that each individual detection tool does intentionally yield a number of false positive detections, but when combined, the false positives tend to be mutually exclusive. This would result in a particularly sensitive and specific detector.

Various other modifications, adaptations, and alternative designs are of course possible in light of the above teachings. Therefore, it should be understood at this time that within the scope of the appended claims the invention might be practiced otherwise than as specifically described herein.

It should be observed that while the foregoing detailed description of various embodiments of the present invention is set forth in some detail, the invention is not limited to those details and an implantable neurostimulator or neurological disorder detection device made according to the invention can differ from the disclosed embodiments in numerous ways. In particular, it will be appreciated that embodiments of the present invention may be employed in many different applications to detect and train the detection of anomalous neurological characteristics in at least one portion of a patient's brain. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

What is claimed is:

1. A method for creating a patient-specific template from at least one record of electrographic signal data stored by an implantable device, the method comprising the steps of:

uploading the at least one record of electrographic signal data from the implantable device to an external apparatus;

processing the at least one record to generate at least one parameter; and forming the patient-specific template from the at at least one parameter by performing a single local minimum variant of a greedy line search.

2. The method for developing a patient-specific template of claim 1, wherein performing a single local minimum variant of a greedy line search comprises the steps of:

selecting a variable parameter from a working parameter set;

adjusting a value of the variable parameter in a first direction and checking a result value until the result value increases or becomes incomputable, or an end of range is reached;

determining whether a local minimum has been identifield, and if not, adjusting a value of the variable parameter in a second direction and checking a result value until the result value increases or becomes incomputable, or an end of range is reached; and identifying a desired value of the variable parameter at which the result value is at a minimum.

3. The method for developing a patient-specific template of claim 2, further comprising the step of selecting the at least one test record as a subset of the at least one record of electrographic signal data.

4. The method for developing a patient-specific template of claim 2, further comprising the step of incorporating the desired value of the variable parameter into the working parameter set.

5. The method for developing a patient-specific template of claim 2, further comprising the steps of:

selecting an initial parameter set; and deriving the working parameter set from the initial parameter set.

6. The method for developing a patient-specific template of claim 5, wherein selecting an initial parameter set comprises the steps of:

employing at least one heuristic algorithm to generate at least one initial parameter; and forming an initial parameter set from the at least one initial parameter.

7. The method or developing a patient-specific template of claim 2, further comprising the step of selecting a termination criterion.

8. The method for developing a patient-specific template of claim 7, further comprising the step of comparing the working parameter set to a stored parameter set.

9. The mothod for developing a patient-specific template of claim 8, wherein the step of comparing the working parameter set to a stored parameter set comprises the steps of:

identifying a plurality of performance factors on the at least one test record;

combining the plurality of performance factors into a working performance metric; and comparing the working performance metric to a stored performance metric corresponding to the stored parameter set.

10. The method for developing a patient-specific template of claim 9, further comprising the step of replacing the stored parameter set with the working parameter set if the working performance metric is better than the stored performance metric.

11. The method for developing a patient-specific template of claim 8, further comprising the step of determining whether the termination criterion is met.

12. The method for developing a patient-specific template of claim 7, further comprising the step of iteratively testing parameter sets to accomplish a multidimensional search by repeating the steps of selecting a parameter, adjusting a value of the variable parameter in a first direction, determining whether a local minimum has been identified, and if not, adjusting a value of the variable parameter in a second direction, and identifying a desired parameter value, for each variable parameter in the working parameter set.

13. The method for developing a patient-specific template of claim 12, wherein the step of iteratively testing parameter sets is performed repeatedly until the termination criterion is met.

14. The method for developing a patient-specific template of claim 13, wherein the termination criterion comprises a convergence bound.

15. The method for developing a patient-specific template of claim 13, wherein the termination criterion comprises a maximum number of iterations.

16. The method for developing a patient-specific template of claim 2, further comprising the step of converting the patient-specific template into a format recognizable by the implantable device.

17. A method for creating a patient-specific template from at least one record of electrographic signal data stored by an implantable device, the method comprising the steps of:
uploading the at least one record of electrographic signal data from the implantable device to an external apparatus;
processing the at least one record to generate at least one parameter; and
forming the patient-specific template from the at least one parameter by calculating a threshold from a feature overlay.

18. The method for developing a patient-specific template of claim 17, wherein calculating a threshold from a feature overlay comprises the steps of:
selecting a feature to be tested on the at least one record;
calculating an overlay feature based on a value of the feature and a trend for the feature on the at least one record; and
identifying a threshold value for the feature based on the overlay feature.

19. The method for developing a patient-specific template of claim 18, further comprising the steps of checking the at least one record for noise or an artifact, and discarding the at least one record if noise or an artifact is present.

20. The method for developing a patient-specific template of claim 18, further comprising the steps of checking a length of the at least one record, and discarding the at least one record the length is too short.

21. The method for developing a patient-specific template of claim 18, further comprising the steps of checking a location of an annotation within the at least one record, and discarding the at least one record if the annotation is too near a beginning or an end of the at least one record.

22. The method for developing a patient-specific template of claim 18, further comprising the step of calculating at least one statistic from the overlay feature.

23. The method for developing a patient-specific template of claim 22, wherein the at least one statistic comprises a maximum value.

24. The method for developing a patient-specific template of claim 23, further comprising the steps of:
determining whether the at least one record is a baseline record type or an event-containing record type; and
updating a statistical value for a category associated with the record type.

25. The method for developing a patient-specific template of claim 24, wherein the statistical value comprises overlay feature maxima.

26. The method for developing a patient-specific template of claim 25, wherein the at least one record is an event-containing record type, and wherein the overlay feature maxima are obtained from a region surrounding an annotation of the at least one record.

27. The method for developing a patient-specific template of claim 26, wherein the region comprises a time band of approximately ±12.8 seconds around an annotation of unequivocal seizure onset.

28. The method for developing a patient-specific template of claim 25, wherein the step of identifying a threshold value for the feature comprises the steps of:
identifying a maximum value of maxima associated with baseline record types;
identifying a minimum value of maxima associated with event-containing record types;
setting a threshold at a desired interval between the minimum value and the maximum value.

29. The method for developing a patient-specific template of claim 28, wherein the desired interval is halfway between the minimum value and the maximum value.

30. The method for developing a patient-specific template of claim 28, wherein the desired interval is 5% between the minimum value and the maximum value.

31. The method for developing a patient-specific template of claim 28, wherein the desired interval is 10% between the minimum value and the maximum value.

32. The method for developing a patient-specific template of claim 29, further comprising the step of rounding the threshold up to a discrete value.

33. The method for developing a patient-specific template of claim 25, wherein the step of identifying a threshold value for the feature comprises the steps of:
identifying a maximum value of maxima associated with baseline record types;
setting a threshold a desired interval higher than the maximum value.

34. The method for developing a patient-specific template of claim 33, wherein the desired interval is 5%.

35. The method for developing a patient-specific template of claim 34, further comprising the step of rounding the threshold up to a discrete value.

36. The method for developing a patient-specific template of claim 18, wherein the overlay feature comprises a difference between the value of the feature and the trend for the feature, and wherein the threshold value comprises a fixed offset threshold.

37. The method for developing a patient-specific template of claim 18, wherein the overlay feature comprises a quotient between the value of the feature and the trend for the feature, and wherein the threshold value comprises a percentage offset threshold.

38. The method for developing a patient-specific template of claim 17, further comprising the step of selecting the at least one test record as a subset of the at least one record of electrographic signal data.

39. The method for developing a patient-specific template of claim 17, further comprising the step of incorporating the desired value of the variable parameter into the working parameter set.

40. The method for developing a patient-specific template of claim 17, further comprising the steps of:
selecting an initial parameter set; and
deriving the working parameter set from the initial parameter set.

41. The method for developing a patient-specific template of claim 40, wherein selecting an initial parameter set comprises the steps of:
employing at least one heuristic algorithm to generate at least one initial parameter; and
forming an initial parameter set from the at least one initial parameter.

42. The method for developing a patient-specific template of claim 17, further comprising the step of converting the patient-specific template into a format recognizable by the implantable device.

43. A method for creating a patient-specific template from at least one record of electrographic signal data stored by an implantable device, the method comprising the steps of:

uploading the at least one record of electrographic signal data from the implantable device to an external apparatus;

determining whether the at least one record is a statistical outlier, and if so, discarding the at least one record;

processing the at least one record to generate at least one parameter; and forming the patient-specific template from the at least one parameter.

44. The method for developing a patient-specific template of claim 43, wherein the step of determining whether the at least one record is a statistical outlier comprises the steps of:

calculating at least one statistic from the record, wherein the at least one statistic comprises a maximum value;

determining whether the at least one record is a baseline record type or an event-containing record type;

updating a plurality of statistical values for a category associated with the record type, wherein the plurality of statistical values comprises a mean, a standard deviation, and a maximum of maxima;

identifying the at least one record as an outlier based on a comparison of the maximum value and at least one of the plurality of statistical values.

45. The method for developing a patient-specific template of claim 44, wherein the identifying step comprises the steps of:

if the at least one record is a baseline record type, identifying the at least one record as an outlier if its maximum value is greater or equal to than two standard deviations above the mean for baseline record types; and if the at least one record is an event-containing record type, identifying the at least one record as an outlier if its maximum is greater than or equal to one standard deviation below the mean or event-containing record types.

46. The method for developing a patient-specific template of claim 44, wherein the identifying step comprises the steps of:

if the at least one record is a baseline record type, identifying the at least one record as an outlier if its maximum value is greater than or equal to two standard deviations above theme for baseline record types; and if the at least one record is an event-containing record type, identifying the at least one record as an outlier if its maximum is greater than or equal to one standard deviation below the mean for event-containing record types and its maximum is lower than the maximum for baseline record types.

47. A method for creating a patient-specific template from at least one record of electrographic signal data stored by an implantable device, the method comprising the steps of:

unloading the at least one record of electrographic signal data from the implantable device to external apparatus;

processing the at least one record to generate at least one parameter for each of a plurality of detection tools; and combining the at least one parameter for each of the plurality of detection tools into a template;

wherein each of the plurality of detection tools has a detection persistence, and wherein the combining step comprises identifying a preferred persistence value for each of the plurality of detection tools.

48. The method for creating a patient-specific template of claim 47, wherein the step of identifying preferred persistence value comprises performing a greedy line search across the plurality of detection tools.

49. The method for creating a patient-specific template of claim 47, wherein the step of identifying preferred persistence value comprises performing a single local minimum variant of a greedy line search across the plurality of detection tools.

50. The method for creating a patient-specific template of claim 47, wherein the step of identifying preferred persistence value comprises performing an exhaustive search across the plurality of detection tools.

51. The method for creating a patient-specific template of claim 47, wherein the combining step further comprises the step of identifying a preferred subset of the plurality of detection tools.

* * * * *